United States Patent

Watanabe

[11] Patent Number: 5,995,217
[45] Date of Patent: Nov. 30, 1999

[54] APPARATUS AND A METHOD FOR MEASURING A DENSITY OF DEFECTS EXISTING IN A SEMICONDUCTOR WAFER AND AN APPARATUS AND A METHOD FOR MEASURING AN INHERENT SCATTERING INTENSITY OF DEFECTS EXISTING IN A SEMICONDUCTOR WAFER

[75] Inventor: Noriko Watanabe, Odawara, Japan

[73] Assignee: Komatsu Electronic Metals Co., Ltd., Kanagawa, Japan

[21] Appl. No.: 09/146,096

[22] Filed: Sep. 3, 1998

[30] Foreign Application Priority Data

Sep. 4, 1997 [JP] Japan ................................. 9-256118

[51] Int. Cl.$^6$ ..................................................... G01N 21/00
[52] U.S. Cl. ........................... 356/237; 356/337; 356/343
[58] Field of Search ...................................... 356/237, 337, 356/343

[56] References Cited

U.S. PATENT DOCUMENTS 5,355,212  10/1994  Wells ..................................... 356/237.4
5,877,860  3/1999   Klein ......................................... 356/347

Primary Examiner—Robert H. Kim
Assistant Examiner—Reginald A. Ratliff
Attorney, Agent, or Firm—Welsh & Katz, Ltd.

[57] ABSTRACT

A laser is irradiated on the surface of a semiconductor wafer while a stage mounted on the semiconductor wafer is moved, and scattering lights emitted from the surface of the semiconductor wafer is received by the receiving device, and an intensity distribution of the scattering lights is measured. The intensity distribution is processed by the controller so as to obtain a defect density of the semiconductor wafer.

16 Claims, 15 Drawing Sheets

APPARATUS AND A METHOD FOR MEASURING A DENSITY OF DEFECTS EXISTING IN A SEMICONDUCTOR WAFER AND AN APPARATUS AND A METHOD FOR MEASURING AN INHERENT SCATTERING INTENSITY OF DEFECTS EXISTING IN A SEMICONDUCTOR WAFER

BACKGROUND OF THE INVENTION

1. Field of the Invention

This invention relates to an apparatus and a method for measuring a density of defects existing in a semiconductor wafer and an apparatus and a method for measuring an inherent scattering intensity of defects existing in a semiconductor wafer, especially relates to an apparatus and a method which are effective to accurately evaluate crystal defects existing in a semiconductor wafer.

2. Description of the Prior Art

It is known the technique in which crystal defects (hereinafter referred to as "defects") existing in a semiconductor wafer is measured by using a laser. In this technique, the defects existing in the semiconductor wafer is measured by performing a series of the following steps.

(1) Irradiating a laser on the surface of a semiconductor wafer, and receiving a scattered light which is scattered by the defects existing in the semiconductor wafer.

(2) Transferring the scattered light received in step1 to the frequency of the defects.

(3) Deciding a detecting possibility depth of the defects by utilizing a attenuation characteristics of the laser.

(4) Calculating a detecting possibility volume of the defects by using the detecting possibility depth deciding in step 3 and the area of irradiating the laser.

(5) Deriving a density of the defects by using the detecting possibility volume calculated in step 4 and the frequency of the defects deriving in step 2.

However, There is a case that the density of the defects obtained by performing the above steps can deviate from the actual density of the defects because the detecting possibility depth is decided as a fixed value. This depends on distributing the defects having various inherent scattering intensitys in the semiconductor wafer. For example, a large defect has an inherent scattering intensity which is larger than that of a small defect, and can be detected in a deeper depth.

Therefore, when a large defect exists in a depth which is deeper than the detecting possibility depth decided previously, the signal obtained from the defect is included in the information of the density. And then the density of the defects which is finally obtained becomes larger than the actual density.

On the other hand, if the detecting possibility depth is greatly set in consideration of the existence of an extra signal like the above-mentioned, the density of the defects which is finally obtained becomes smaller than the actual density because a small defect cannot be detected even if existing in the set depth.

Thus, it is difficult to decide the detecting possibility depth in the above conventional technology, and it is necessary to improve the conventional technology in order to accurately evaluate the defects.

SUMMARY OF THE INVENTION

This invention is created in order to provide an apparatus and a method for measuring a density of defects existing in a semiconductor wafer and an apparatus and a method for measuring an inherent scattering intensity of defects existing in a semiconductor wafer which are effective to accurately evaluate crystal defects existing in a semiconductor wafer.

The feature of this invention is in assumption that the defects existing in the semiconductor have the same size, the application of intensity of the scattered light measured by scanning the laser to the attenuation curve of the laser, and the decision of depths where the defects exist.

According to the above construction, the difference of the inherent scattering intensity among each defect is expressed as a difference of depth where each of the defects exists. As a result, even when the defects with different size are distributed in the semiconductor, an accurate defect density can be obtained (Refer to FIG. 1).

BRIEF DESCRIPTION OF THE DRAWINGS

The various features of novelty which characterize this invention are pointed out with particularity in the claims annexed to and forming a part of this specification. For a better understanding of this invention, its operating advantages, and specific objects attained by its use, reference should be had to the accompanying drawing and descriptive matter in which there is illustrated and described a preferred embodiment of this invention.

This invention disclosed herein will be understood better with reference to the following drawings.

DETAILED DESCRIPTION OF THE INVENTION (The First Mode)

The first mode of this invention concerns measuring a density of defects. Generally, defects exist in the semiconductor with different size and various depth. It is necessary to consider the depth and the inherent scattering intensity of each defect in order to obtain the density of the defects which exist with such different size and various depth.

It is difficult to directly measure the depth and inherent scattering intensity of each defect existing in the semiconductor by using the current technology. Having considered such difficulty, the inventor of this invention proposes the model in which the defects distribute homogeneously in a constant volume with the same size, and aims the deriving an accurate density of the defects.

As a rule, as for the size of the defects which exist in the semiconductor, it is often dispersion of about several tens of nano meter. Especially, because the grown-defects is formed as the same size approximately, the defect distribution in the semiconductor can be expressed by using the above model.

The first mode of this invention is constructed in view of the above aspect, and provides the technique for accurately obtaining the density of the defects existing in the semiconductor.

Figure 1:
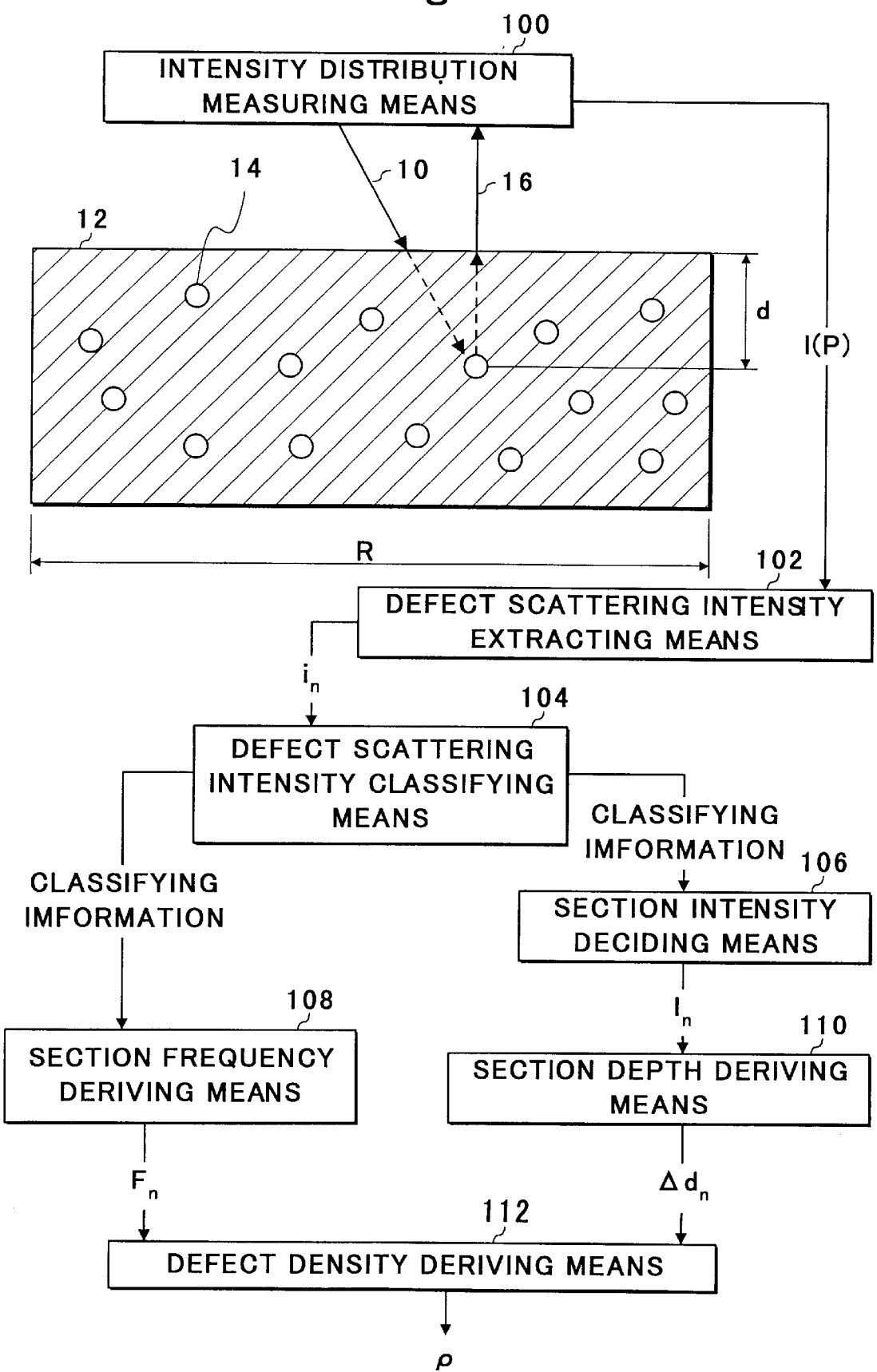
FIG. 1 is a conception diagram which shows the construction of the apparatus for measuring a density of defects in accordance with the first mode of this invention.

FIG. 1 is a conception diagram which shows the construction of the apparatus for measuring a density of defects in accordance with the first mode of this invention. Hereafter, the construction of the first mode of this invention is explained by using this figure.

The semiconductor 12 is a crystal composed of silicon, germanium and so on. This semiconductor 12 is used in industry in the form like the silicon wafer and the silicon substrate, etc.

The defects 14 are crystal defects formed in the semiconductor 12, and distribute in the semiconductor 12 with various depths as shown in this figure. These defects 14 have various sizes respectively, the larger size is, the larger inherent scattering intensity is. In this specification, a depth where the defect 14 exists is defined as the defect depth d.

The laser 10 is irradiated to the surface of the semiconductor 12, and is used for detecting the defects 14 existing in the semiconductor 12. The laser 10 decreases while it travels in the semiconductor 12. The attenuation characteristic of the laser 10 is determined with its wave length and the composition element of the semiconductor 12. A variety of the research result has been reported, and the attenuation characteristic of the laser 10 is widely used as a well-known technology. This invention uses this attenuation characteristic of the laser 10. The explanation of this characteristic is described later.

The scattered light 16 is a component of the light which is generated by the laser's colliding with the defects 14. When the laser 10 collides with the defects 14, it is scattered in proportion to the size of the colliding defect 14, and the part is emitted from the surface of the semiconductor 12. In this invention, The scattered light 16 which is emitted from the surface of the semiconductor 12 is measured, and is used in order to derive the defect density. The scattered light 16 decreases as well as the laser 10 while it travels in the semiconductor 12. Therefore, as the defect depth d increases, the laser 10 and the scattered light 16 decrease. As a result of which, the signal which is emitted from the surface of the semiconductor 12 becomes small.

The intensity distribution measuring means 100 is means for measuring the intensity distribution of the scattered light 16 which is obtained from the defects 14 existing in a measuring region R of the semiconductor 12 by scanning the measuring region R with the laser 10. The intensity distribution measuring means 100 repeats irradiating of the laser 10 and receiving of the scattered light 16 in the measuring region R of the semiconductor 12, and detects the defect distribution in the measuring region R as the intensity distribution of the scattered light 16. It is desirable to assume actual measuring area R to be a plane though scanning measuring area R is shown in the one dimensional because the structure of the semiconductor 12 is shown in the cross section in this figure.

Figure 2:
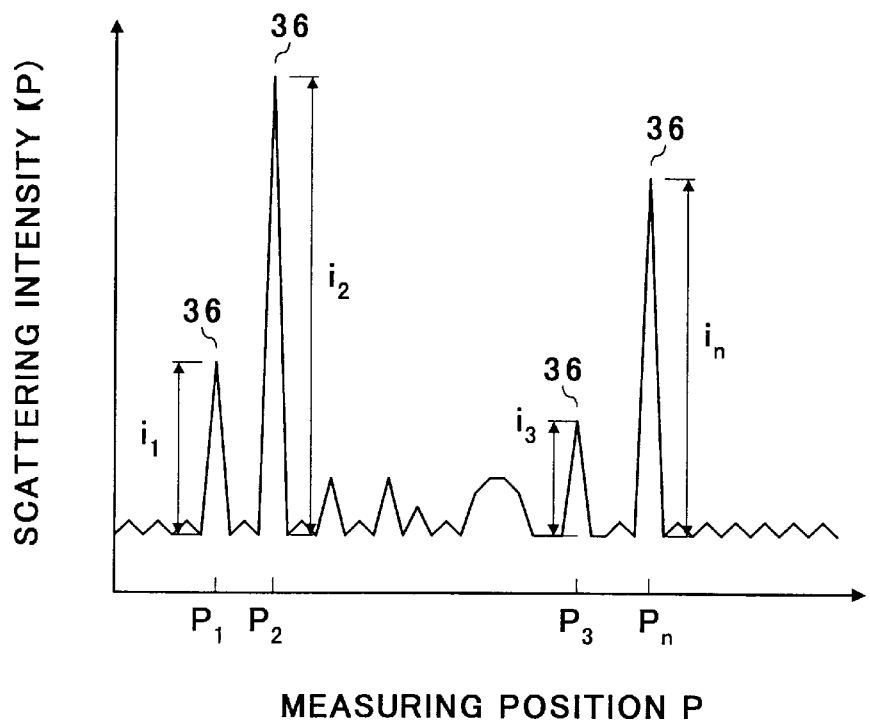
FIG. 2 is a conception diagram which shows the intensity distribution of the scattered light 16 measured by the intensity distribution measuring means 100 and extracting the scattering intensity of the defects.

FIG. 2 is a conception diagram which shows the intensity distribution of the scattered light 16 measured by the intensity distribution measuring means 100 and extracting the scattering intensity of the defects.

The graph shown in this figure supposes the intensity distribution in case that the measuring position of the semiconductor 12 is set in a horizontal axis and the intensity of the scattered light 16 received in the measuring position is set in a vertical axis. As shown in this figure, the intensity of the scattered light 16 emitted from the surface of the semiconductor 12 varies in proportion to the measuring position of the semiconductor 12, and becomes a signal having a certain distribution when the measuring region R is observed as a whole. The reason for this is that the intensity distribution measuring means 100 detects the scattered light from the defects with different size existing in the semiconductor 12 in various depths.

The defect scattering intensity extracting means 12 is means for extracting the defect scattering intensity 36 from the intensity distribution measured by the intensity distribution measuring means 100. As shown in FIG. 2, The extracting of the defect scattering intensity 36 is conducted by selecting the signal peaks which can be thought to originate in the defects from the intensity distribution measured by the intensity distribution measuring means 100. For instance, the scattering intensities $i_1$, $i_2$, $i_3$, . . . $i_n$ at measurement positions $P_1$, $P_2$, $P_3$, . . . $P_n$ are assumed to be the defect scattering intensities 36 in the example shown in FIG. 2.

The defect scattering intensity classifying means 104 is means for classifying the defect scattering intensity 36 extracted by the defect scattering intensity extracting means 102 into plural sections with the section range ΔI. This defect scattering intensity classifying means 104 classifies the defect scattering intensity 36 extracted by the defect scattering intensity extracting means 102 according to the intensity with the section range ΔI. For example, the section range ΔI is set to be 10, and the intensities of 0 to 10 are classified as the first section, the intensities of 10 to 20 are classified as the second section. The defect scattering intensity classifying means 104 outputs the classifying information to the section intensity deciding means 106 and section frequency deriving means 108.

The section intensity deciding means 106 is means for deciding the section intensities $I_n$ of each section classified by the defect scattering intensity classifying means 104. The deciding of the section intensities $I_n$ may be conducted by using the average value, the minimum value, or the maximum value of the intensities classified in each of the sections. The decision criteria of the section intensities $I_n$ are unified in each the section.

The section frequency deriving means 108 is means for deriving the section frequencies $F_n$ in each of the sections classified by the defect scattering intensity classifying means 104. For example, the peaks of the defect scattering intensity 36 shown in FIG. 2 are assumed to be one frequency, and the section frequencies $F_n$ are obtained by tabulating the frequencies in each of the sections classified by the defect scattering intensity classifying means 104.

Figure 3:
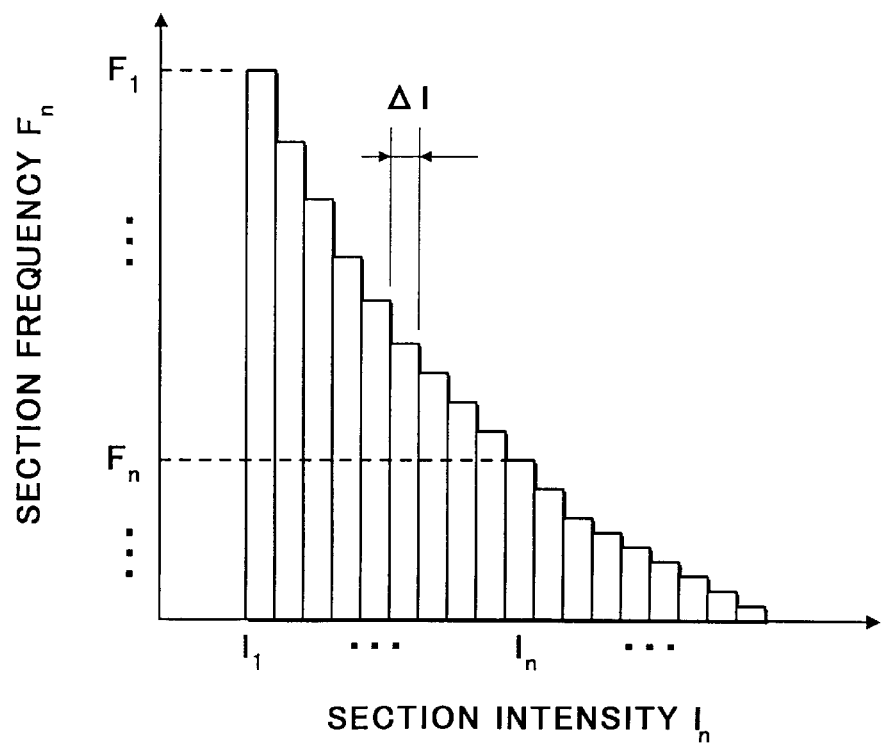
FIG. 3 is a conception diagram which shows the section frequency $F_n$ derived by the section frequency deriving means 108.

FIG. 3 is a conception diagram which shows the section frequency $F_n$ derived by the section frequency deriving means 108. This figure expresses the section frequencies $F_n$ derived by the section frequency deriving means 108 as a histogram. As shown in this figure, the defect scattering intensity 36 extracted by the defect scattering intensity extracting means 102 can be expressed as the relation between the section intensities and the section frequencies.

The section depth deriving means 110 is means for deriving the section depths $\Delta d_n$ in each of the sections by applying the section intensities $I_n$ decided by the section intensity deciding means 106 to the attenuation curve 18 of the laser 10.

Figure 4:
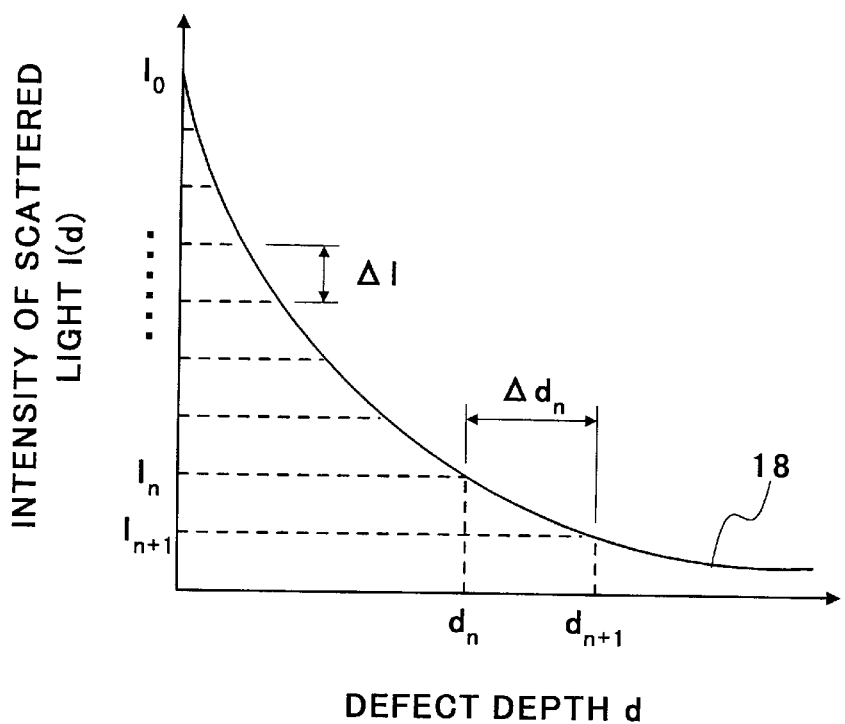
FIG. 4 is a graph which shows the attenuation curve of the laser 10.

FIG. 4 is a graph which shows the attenuation curve of the laser 10. The attenuation curve 18 shown in this figure is a graph which shows the relation between the defect depth d and the scattering intensity, in which the decrease of the laser 10 entered the inside of the semiconductor 12 and the decrease of the scattered light 16 generated by the laser's colliding with the defects 14 are considered. The attenuation curve 18 can be defined by the following numerical expression.

(Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser.

Here, the penetration depth α of the laser is called the linear absorption coefficient, and is a value decided by the composition element of the semiconductor and its composition as explained above.

Figure 5:
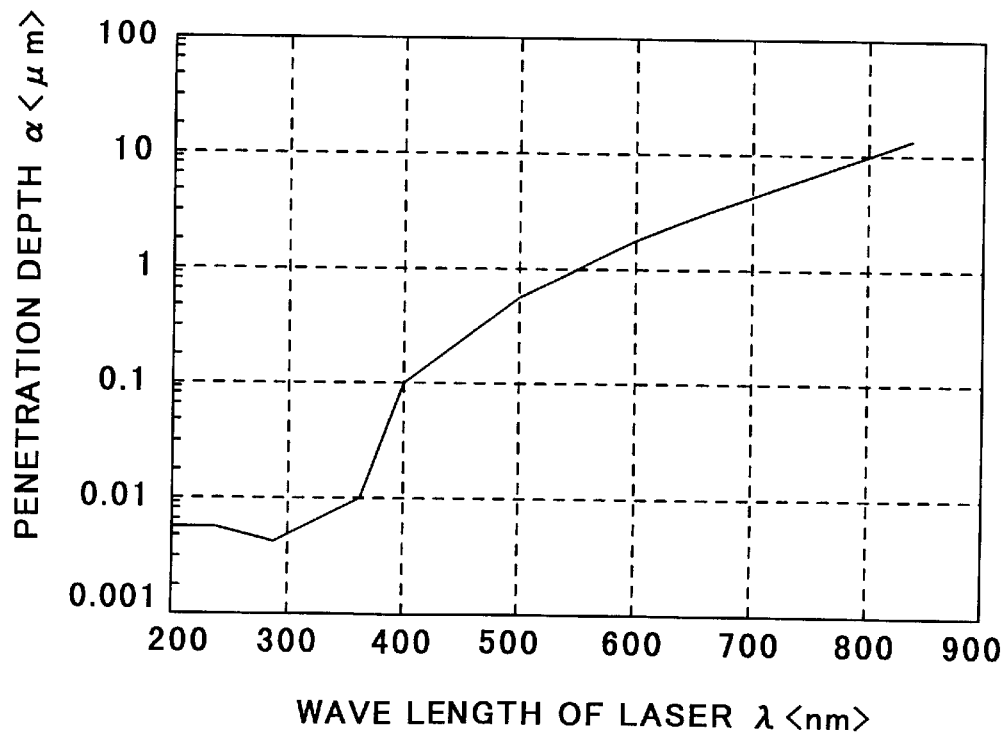
FIG. 5 is a graph which shows the relation between the wave length $\lambda$ and penetration depth of the laser.

FIG. 5 is a graph which shows the relation between the wave length λ and penetration depth of the laser. The graph shown in this figure shows the penetration depth in case that the semiconductor 12 is composed of silicon. For example, if the laser of 800 nm in wave length is irradiated to the silicon, the laser travels up to the depth of 10 μm while decreasing by the characteristic shown in expression 1.

The section depth deriving means 110 obtains the defect depths corresponding to the section intensities $I_n$ decided by the section intensity deciding means 106, and assumes them to the section depths $\Delta d_n$. The differentiation or the difference operation of the attenuation curve 18 is thought as a deriving method of the section depths $\Delta d_n$. Hereafter, these methods are referred as the differentiation type deriving method and the difference type deriving method, and these methods are explained as follows.

1. Differentiation Type Deriving Method

The section depths $\Delta d_n$ are derived by performing the following steps in the differentiation type deriving method.

(1) Differentiating the attenuation curve 18, and obtaining the following numerical expression.

(Expression 13)

$$\frac{\partial}{\partial d} \cdot I(d) = -\frac{2}{\alpha} \cdot I_0 \cdot \exp\left(-\frac{2}{\alpha} \cdot d\right) \quad (13)$$

The value obtained by the above numerical expression shows the gradient of the attenuation curve 18.

(2) Obtaining the following numerical expression based on the thought in which the product of the gradient of the attenuation curve 18 and the section depths $\Delta d_n$ is the section range ΔI.

(Expression 14)

$$\Delta I = \frac{2}{\alpha} \cdot I_0 \cdot \exp\left(-\frac{2}{\alpha} \cdot d\right) \cdot \Delta d_n \quad (14)$$

Here, when the attenuation curve 18 is differentiated, the sign of the minus is appeared. But this sign of the minus can be deleted in the above numerical expression because the section range ΔI is the absolute value.

(3) Deriving the following numerical expression by expanding the expression 14 in the shape of "$\Delta d_n=$".

(Expression 15)

$$\Delta d_n = \frac{\alpha \cdot \Delta I}{2 \cdot I_0 \cdot \exp\left(-\frac{2}{\alpha} \cdot d\right)} \quad (15)$$

Here, deriving the following numerical expression in that the right side of expression 1 is included in the denominator of the above expression.

(Expression 16)

$$\Delta d_n = \frac{\alpha \cdot \Delta I}{2 \cdot I(d)} \quad (16)$$

Here, I(d) is the scattering intensity of the defect existing in the depth d.

(4) Obtaining the following numerical expression based on the thought that the scattering intensity of the defect existing in the depth d is equivalent to the section intensities $I_n$ corresponding to the section depths $\Delta d_n$.

(Expression 2)

$$\Delta d_n = \frac{\alpha \cdot \Delta I}{2 \cdot I_n} \quad (2)$$

The value obtained by solving the above expression is the section depths $\Delta d_n$.

2. Difference Type Deriving Method

The section depths $\Delta d_n$ are derived by performing the following steps in the difference type deriving method.

(1) According to the attenuation curve 18 of the laser 10, the defect depths $d_n$ corresponding to the section intensities $I_n$ can be expressed as the following numerical expression.
(Expression 17)

$$I_n = I_0 \cdot \exp\left(-\frac{2}{\alpha} \cdot d_n\right) \tag{17}$$

The section depth in the section n is related to the defect depth by the above expression.

(2) Deriving the following numerical expression by expanding expression 17 in the shape of "$d_n=$".
(Expression 18)

$$d_n = -\frac{\alpha}{2} \cdot \text{Ln}\left(\frac{I_n}{I_0}\right) \tag{18}$$

The defect depth in the section n is obtained by the above expression.

(3) Expressing the defect depth $d_{n+1}$ corresponding to the section intensity $I_{n+1}$ as the following numerical expression based on the attenuation curve 18 of the laser 10.
(Expression 19)

$$I_{n+1} = I_0 \cdot \exp\left(-\frac{2}{\alpha} \cdot d_{n+1}\right) \tag{19}$$

The section depth in the section n+1 is related to the defect depth by the above expression.

(4) Deriving the following numerical expression by expanding expression 19 in the shape of "$d_{n+1}=$".
(Expression 20)

$$d_{n+1} = -\frac{\alpha}{2} \cdot \text{Ln}\left(\frac{I_{n+1}}{I_0}\right) \tag{20}$$

The defect depth in the section n+1 is obtained by the above expression.

(5) Deriving the following numerical expression based on the thought that the section depth $\Delta d_n$ is difference between the defect depth $d_n$ and the defect depth $d_{n+1}$ as shown in FIG. 5.
(Expression 21)

$$\Delta d_n = d_{n+1} - d_n \tag{21}$$

$$= -\frac{\alpha}{2} \cdot \text{Ln}\left(\frac{I_{n+1}}{I_0}\right) + \frac{\alpha}{2} \cdot \text{Ln}\left(\frac{I_n}{I_0}\right)$$

And deriving the following numerical expression by expanding the above expression.
(Expression 3)

$$\Delta d_n = \frac{\alpha}{2} \cdot \text{Ln} \cdot \left(\frac{I_n}{I_n - \Delta I}\right) \tag{3}$$

The value obtained by solving the above expression is the section depths $\Delta d_n$.

The section depth deriving means 110 obtains the section depths $\Delta d_n$ by performing the differentiation type deriving method or the difference type deriving method, and outputs the section depths $\Delta d_n$ to the defect density deriving means 112.

The defect density deriving means 112 is means for deriving the defect density ρ by using the section frequencies $F_n$ obtained by the section frequency deriving means 108 and the section depths $\Delta d_n$ obtained by the section depth deriving means 110. If the section depths $\Delta d_n$ in each of the sections are obtained, the volumes can be obtained from the area of the measuring region R. Therefore, the defect densities in each of the sections are obtained by dividing the section frequencies $F_n$ by the obtained volumes.

The defect densities in each of the sections obtained thus show the defect densities in a minute areas respectively. Therefore, they are able to use for data in order to decide the defect density ρ of the measuring region R. The defect density deriving means 112 decides the defect density ρ by using the data obtained thus for example an average of data.

The apparatus for measuring a defect density in accordance with the first mode of this invention explained above can be constructed as a method of measuring the defect density.

Figure 6:
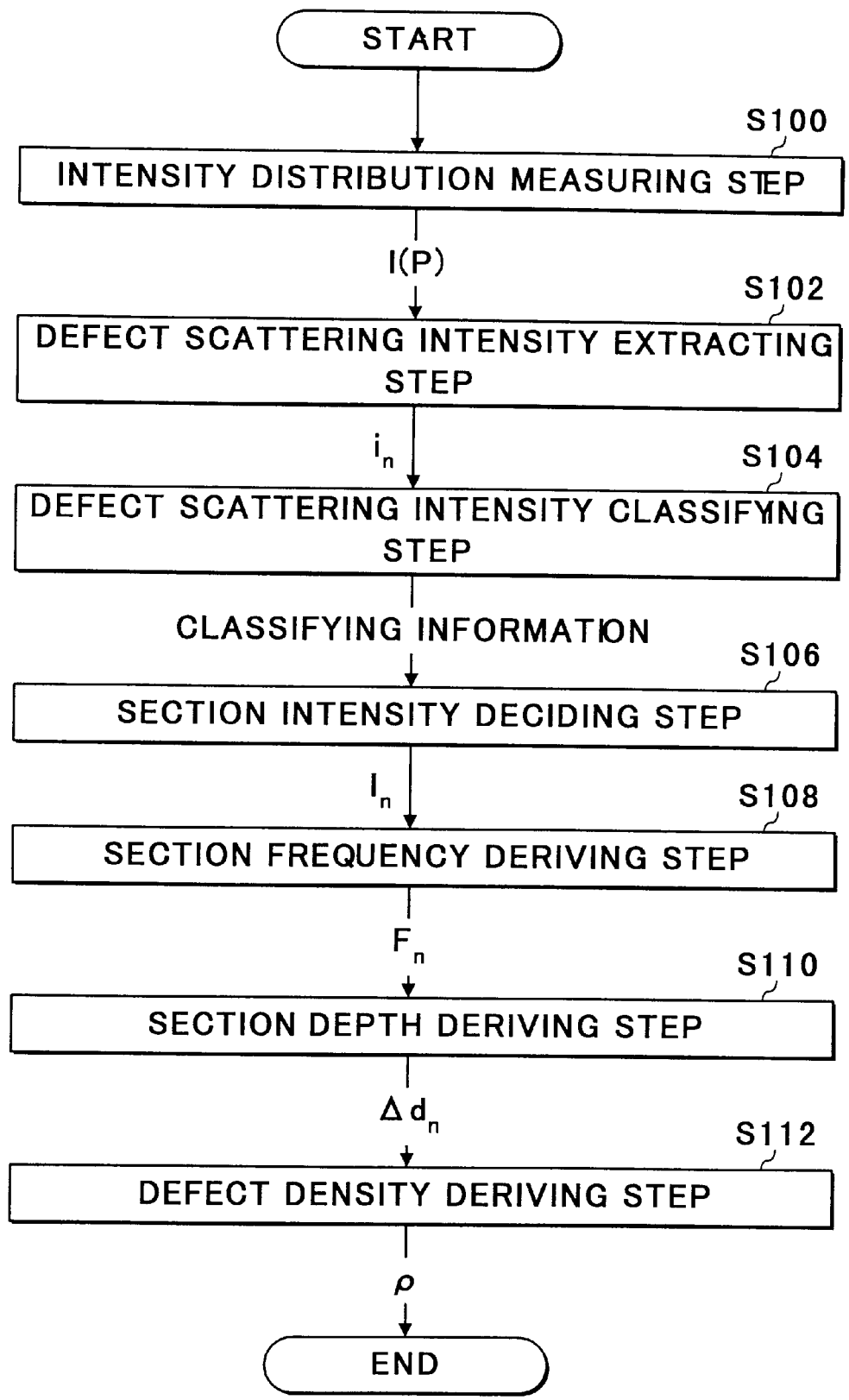
FIG. 6 is a flow chart which shows the construction of the method of measuring a density of defects in accordance with the first mode of this invention.

FIG. 6 is a flow chart which shows the construction of the method of measuring a density of defects in accordance with the first mode of this invention. Hereafter, the construction of the method of measuring a defect density in accordance with the first mode of this invention is explained by using this figure.

The intensity distribution measuring step S100 corresponds to the intensity distribution measuring means 100, in the same way, the defect scattering intensity extracting step S102 corresponds to the defect scattering intensity extracting means 102, the defect scattering intensity classifying step S104 corresponds to the defect scattering intensity classifying means 104, the section intensity deciding step S106 corresponds to the section intensity deciding means 106, the section frequency deriving step S108 corresponds to the section frequency deriving means 108, the section depth deriving step S110 corresponds to the section depth deriving means 110, and the defect density deriving step S112 corresponds to the defect density deriving means 112.

The construction shown in this figure is performed as the following steps.

(1) Irradiating the laser 10 to the surface of the semiconductor 12 (intensity distribution measuring step S100).

(2) Receiving the scattered light 16 emitted from the surface of the semiconductor 12 by irradiating the laser 10 (intensity distribution measuring step S100).

(3) Repeating the step 1 and step 2 while the irradiating position of the laser 10 is varied, and measuring the intensity distribution of the measuring region R by scanning in the measuring region R (intensity distribution measuring step S100).

(4) Extracting the defect scattering intensities 36 from the intensity distribution measured in the intensity distribution measuring step S100 (defect scattering intensity extracting step S102).

(5) Classifying the defect scattering intensities 36 extracted in the defect scattering intensity extracting step S102 with the section range $\Delta I$ (defect scattering intensity classifying step S104).

(6) Deciding the section intensities based on the classifying result in the defect scattering intensity classifying step S104 (section intensity deciding step S106).

(7) Obtaining the section frequencies based on the classifying result in the defect scattering intensity classifying step S104 (section frequency deriving step S108).

(8) Obtaining the section depths $\Delta d_n$ in each of the sections by executing the expression 2 or the expression 3 (section depth deriving step S110).

(9) Obtaining the defect density ρ by using the section frequencies $F_n$ obtained in the section frequency deriving step S108 and the section depths $\Delta d_n$ obtained in the section depth deriving step S110 (defect density deriving step S112)

According to the first mode of this invention, because the defect density is decided based on the attenuation curve of the laser, even if the defects with different size exist, the defect density can be measured accurately.

(The Second Mode)

The second mode of this invention is a invention which obtains the defect density by utilizing the linear approximation. As shown in the first mode of this invention explained above, the defect density of the semiconductor can be obtained from the section frequencies $F_n$ and the section depths $\Delta d_n$. The inventor of this invention studies the first mode of this invention in detail, and creates the method of obtaining the defect density by using the geometrical technique. This method is based on the idea that the linear approximation can be applied to the section frequencies $F_n$ in the case that the relation between the attenuation curve of the laser and the defect frequency is expanded mathematically.

The second mode of this invention is constructed in view of the above aspect, and provides the technique of obtaining the defect density of semiconductor geometrically.

Figure 7:
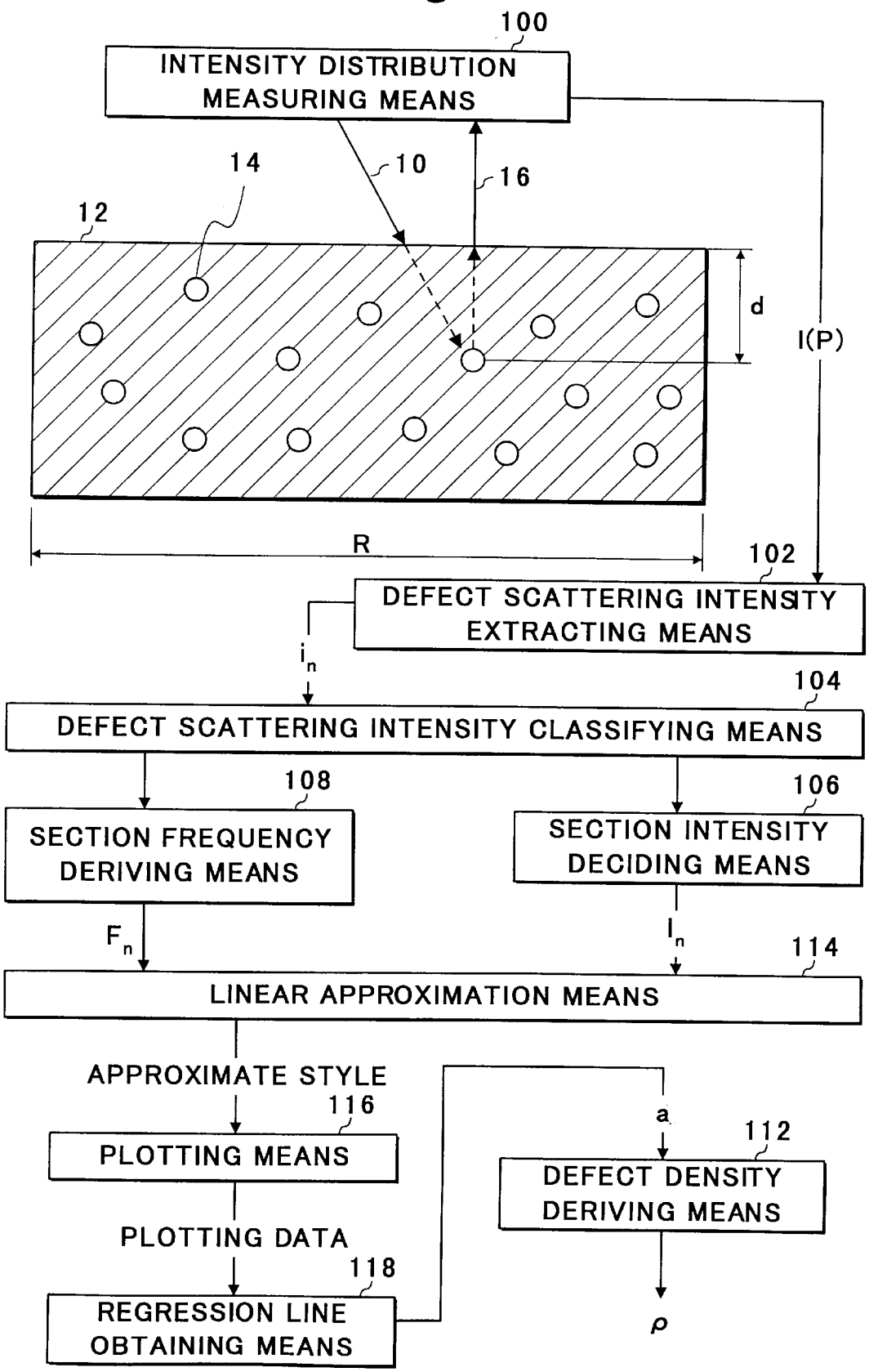
FIG. 7 is a conception diagram which shows the construction of the apparatus for measuring a density of defects in accordance with the second mode of this invention.

FIG. 7 is a conception diagram which shows the construction of the apparatus for measuring a density of defects in accordance with the second mode of this invention. Hereafter, the construction of the second mode of this invention is explained by using this figure.

The explanations of the intensity distribution measuring means 100, the section intensity deciding means 106 and section frequency deriving means 108 are omitted because these means are the same as those of the first mode of this invention.

The linear approximation means 114 is means for applying the linear approximation to the section frequencies $F_n$ obtained by the section frequency deriving means 108 by applying the section intensities $I_n$ in each of the sections decided by the section intensity deciding means 106 to the attenuation curve 18 of the laser 10. The linear approximation of the section frequencies $F_n$ is conducted according to the following steps.

(1) Expressing the section frequency $F_n$ as the following numerical expression.
(Expression 22)

$$F_n = \Delta d_n \cdot S \cdot \rho \quad (22)$$

Here, S is the area of the measuring region R which is known value.

(2) Expressing the section depths $\Delta d_n$ in expression 22 as the function of the section intensities $I_n$ by using the differentiation type deriving method or the difference type deriving method as explained in the first mode of this invention. Expression 22 becomes the following numerical expression in case that the section depths $\Delta d_n$ is derived by the difference type deriving method.
(Expression 23)

$$F_n = \frac{\alpha \cdot S \cdot \rho \cdot \Delta I}{2} \cdot \frac{1}{I_n} \quad (23)$$

The above expression is obtained by substituting expression 2 for expression 22.

On the other hand, expression 22 becomes the following numerical expression in case that the section depths $\Delta d_n$ is derived by the differentiation type deriving method.

(Expression 24)

$$F_n = \frac{\alpha \cdot S \cdot \rho}{2} \cdot \operatorname{Ln} \cdot \left( \frac{I_n}{I_n - \Delta I} \right) \quad (24)$$

The above expression is obtained by substituting expression 3 for expression 22.

(3) Applying any of the following approximate styles to expression 23 or expression 24.
(Expression 4)

$$y = ax + b \quad (4)$$

(Expression 7)

$$y = ax \quad (7)$$

The difference between the approximate style of expression 4 and the approximate style of expression 7 is assuming the y-intercept to be zero, and these styles may be applied.

The plotting means 116 is means for plotting the approximate result by the linear approximation means 114 as the plotting data on the xy plane. The x axis of expression 23 of the differentiation type applied expression 4 or expression 7 can be expressed as the following numerical expression.
(Expression 5)

$$x = \frac{1}{I_n} \quad (5)$$

In the above case, the plotting means 116 plots the values obtained by solving the above expression on the x axis of the xy plane, and plots the section frequencies $F_n$ on the y axis of the xy plane.

On the other hand, the x axis of expression 24 of the differentiation type applied expression 4 or expression 7 can be expressed as the following numerical expression.
(Expression 8)

$$x = \frac{I_n}{I_n - \Delta I} \quad (8)$$

In the above case, the plotting means 116 plots the values obtained by solving the above expression on the x axis of the xy plane, and plots the section frequencies $F_n$ on the y axis of the xy plane.

The regression line obtaining means 118 is means for obtaining the regression line of the plotting data plotted by the plotting means 116. The regression line may be obtained by drawing or approximate calculation.

Figure 8:
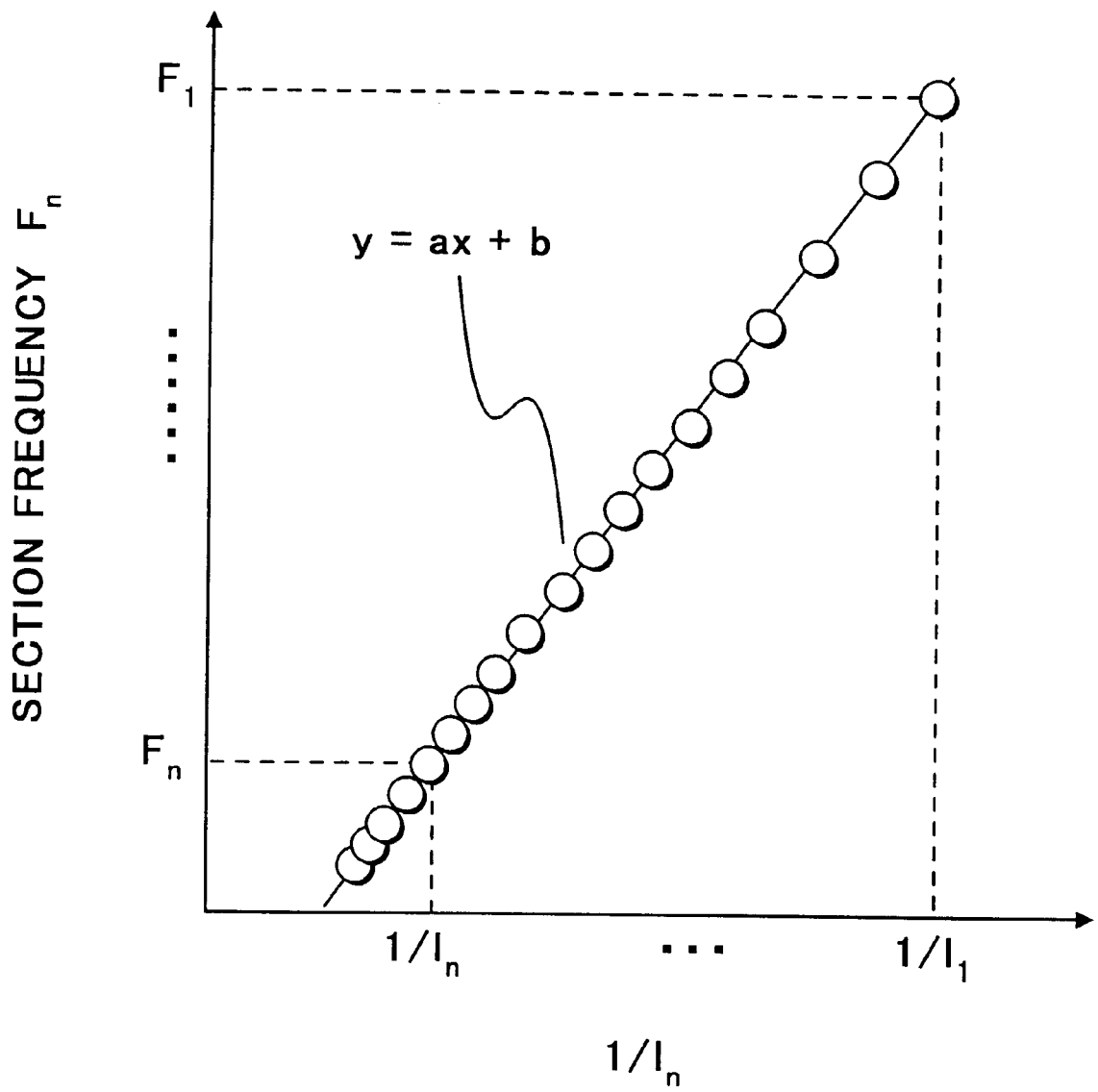
FIG. 8 is a conception diagram which shows the plotting data obtained by using the differentiation type deriving method and linear approximation by which the y-intercept is considered and shows the regression line of the plotting data.

FIG. 8 is a conception diagram which shows the plotting data obtained by using the differentiation type deriving method and linear approximation by which the y-intercept is considered and shows the regression line of the plotting data. As shown in this figure, the regression line is obtained by the condition of the origin of the xy plane not passing in case that the style of "y=ax+b" is used.

Figure 9:
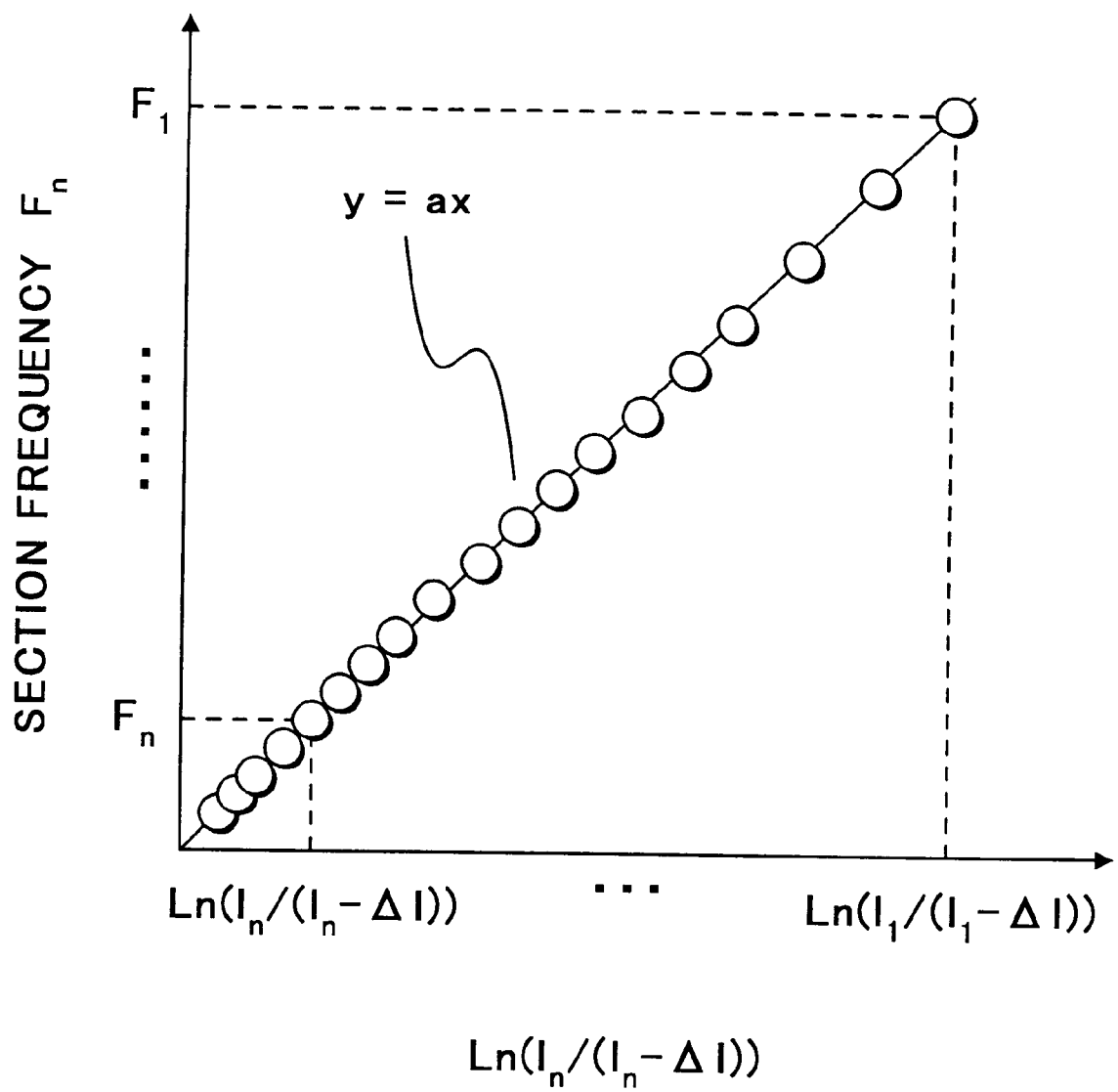
FIG. 9 is a conception diagram which shows the plotting data obtained by using the difference type deriving method and linear approximation by which the y-intercept is zero and shows the regression line of the plotting data.

FIG. 9 is a conception diagram which shows the plotting data obtained by using the difference type deriving method and linear approximation by which the y-intercept is zero and shows the regression line of the plotting data. As shown in this figure, the regression line is obtained by the condition of the origin of the xy plane passing in case that the style of "y=ax" is used.

The defect density deriving means 112 is means for deriving the defect density ρ by using the gradient of the regression line obtained by the regression line obtaining means 118. Here, the gradient a' of the regression line is equal to the gradient a of the linear approximation, and can be expressed as the following numerical expression.
(Expression 25)

$$a' = \frac{\alpha \cdot S \cdot \rho \cdot \Delta I}{2} \quad (25)$$

The above expression is derived based on expression 23.
On the other hand, the gradient a' of the regression line can be expressed as the following numerical expression.
(Expression 26)

$$a' = \frac{\alpha \cdot S \cdot \rho}{2} \quad (26)$$

The above expression is derived based on expression 24.
Therefore, the defect density ρ can be obtained by using the following numerical expression in the differentiation type.
(Expression 6)

$$\rho = \frac{2a'}{\alpha \cdot S \cdot \Delta I} \quad (6)$$

In the above case, the defect density deriving means 112 assumes the value obtained by solving the above expression to be the defect density ρ.

On the other hand, the defect density ρ can be obtained by using the following numerical expression in the difference type.
(Expression 9)

$$\rho = \frac{2a'}{\alpha \cdot S} \quad (9)$$

In the above case, the defect density deriving means 112 assumes the value obtained by solving the above expression to be the defect density ρ.

The apparatus for measuring a defect density in accordance with the second mode of this invention can be constructed as a method of measuring a defect density.

Figure 10:
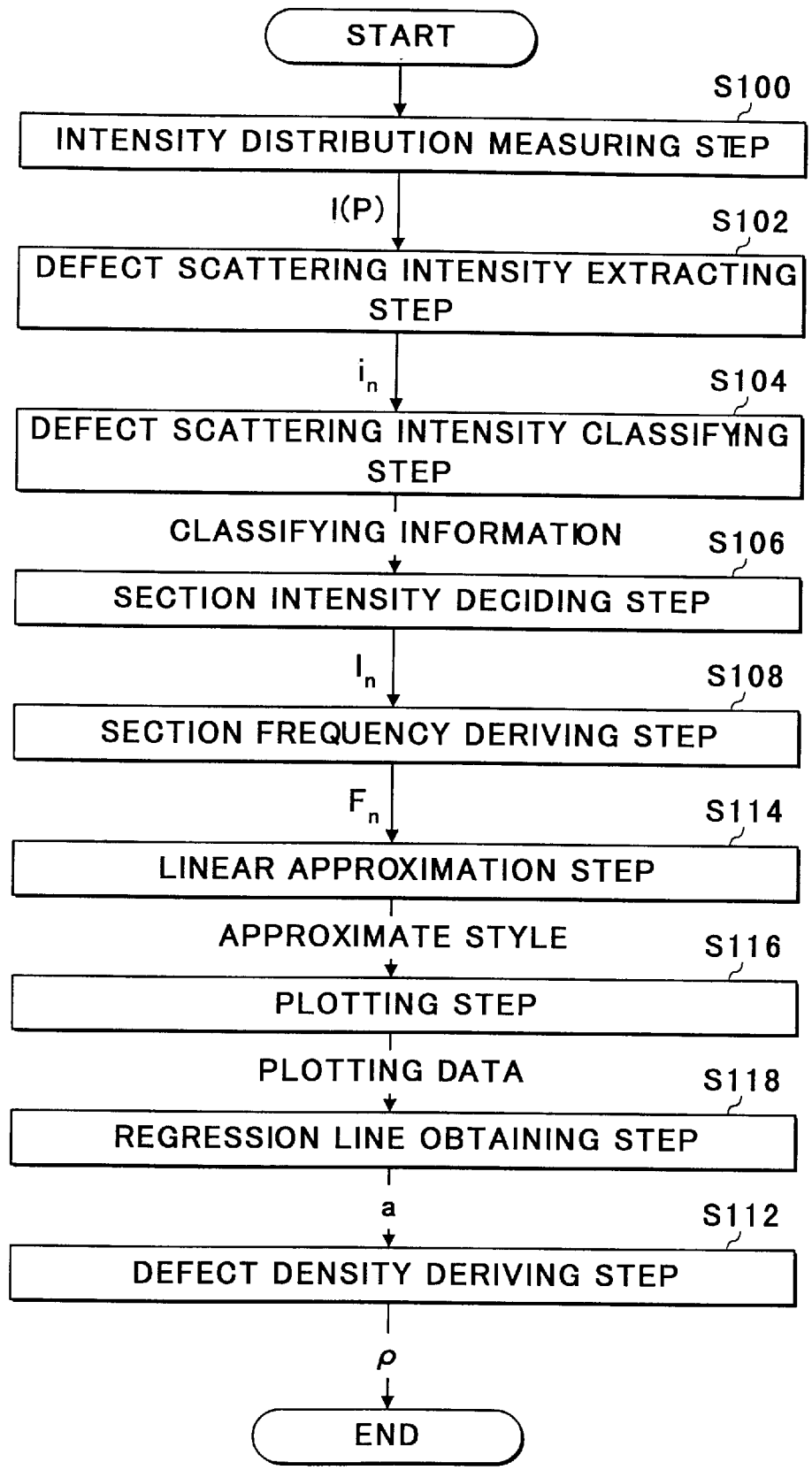
FIG. 10 is a flow chart which shows the construction of the method of measuring a density of defects in accordance with the second mode of this invention.

FIG. 10 is a flow chart which shows the construction of the method of measuring a density of defects in accordance with the second mode of this invention. Hereafter, the construction of the method of measuring a defect density in accordance with the second mode of this invention is explained by using this figure.

The intensity distribution measuring step S100 corresponds to the intensity distribution measuring means 100, in the same way, the defect scattering intensity extracting step S102 corresponds to the defect scattering intensity extracting means 102, the defect scattering intensity classifying step S104 corresponds to the defect scattering intensity classifying means 104, the section intensity deciding step S106 corresponds to the section intensity deciding means 106, the section frequency deriving step S108 corresponds to the section frequency deriving means 108, the linear approximation step S114 corresponds to the linear approximation means 114, the plotting step S116 corresponds to the plotting means 116, the regression line obtaining step S118 corresponds to the regression line obtaining means 118, and the defect density deriving step S112 corresponds to the defect density deriving means 112.

The construction shown in this figure is performed as the following steps.

(1) Irradiating the laser 10 to the surface of the semiconductor 12 (intensity distribution measuring step S100).

(2) Receiving the scattered light 16 emitted from the surface of the semiconductor 12 by irradiating the laser 10 (intensity distribution measuring step S100).

(3) Repeating the step 1 and step 2 while the irradiating position of the laser 10 is varied, and measuring the intensity distribution of the measuring region R by scanning in the measuring region R (intensity distribution measuring step S100).

(4) Extracting the defect scattering intensities 36 from the intensity distribution measured in the intensity distribution measuring step S100 (defect scattering intensity extracting step S102).

(5) Classifying the defect scattering intensities 36 extracted in the defect scattering intensity extracting step S102 with the section range ΔI (defect scattering intensity classifying step S104).

(6) Deciding the section intensities based on the classifying result in the defect scattering intensity classifying step S104 (section intensity deciding step S106).

(7) Obtaining the section frequencies based on the classifying result in the defect scattering intensity classifying step S104 (section frequency deriving step S108).

(8) Applying the linear approximation to the section frequencies $F_n$ in the style of expression 4 or expression 7 (linear approximation step S114).

(9) Obtaining the coordinate on the xy plane based on the approximate result obtained in the linear approximation step S114. That is, the values obtained by executing expression 5 or expression 8 are plotted on the x axis of the xy plane, and the section frequencies are plotted on the y axis of the xy plane (plotting step S116).

(10) Obtaining the regression line of the data plotted on the xy plane in the plotting step S116 (regression line obtaining step S118).

(11) Obtaining the gradient of the regression line obtained in the regression line obtaining step S118, and calculating the defect density ρ by substituting the obtained gradient for expression 6 or expression 9 (defect density deriving step S112).

According to the second mode of this invention, because the section frequencies $F_n$ is processed geometrically, the defect density ρ can be obtained accurately. Incidentally, because the attenuation curve of the laser is considered in this second mode of this invention as well as the first mode of this invention, the defect depth is appropriately determined.

(The Third Mode)

The third mode of this invention concerns measuring the defect inherent scattering intensity. As described above, the inherent scattering intensity of the defect is determined by the defect size. Therefore, the defect size can be predicted if the inherent scattering intensity is obtained. The technique of predicting the defect size has been desired, and will be efficiently utilized in the evaluation of the defect. Here, The inherent scattering intensity of the defect is equivalent to the scattering intensity in case that the decrease of the laser is not considered. The inventor of this invention applies the fact to the geometric method explained in the second mode, and creates the method of obtaining the inherent scattering intensity of the defect.

The third mode of this invention is constructed in view of the above aspect, and provides the technique of obtaining the inherent scattering intensity of the defect.

Figure 11:
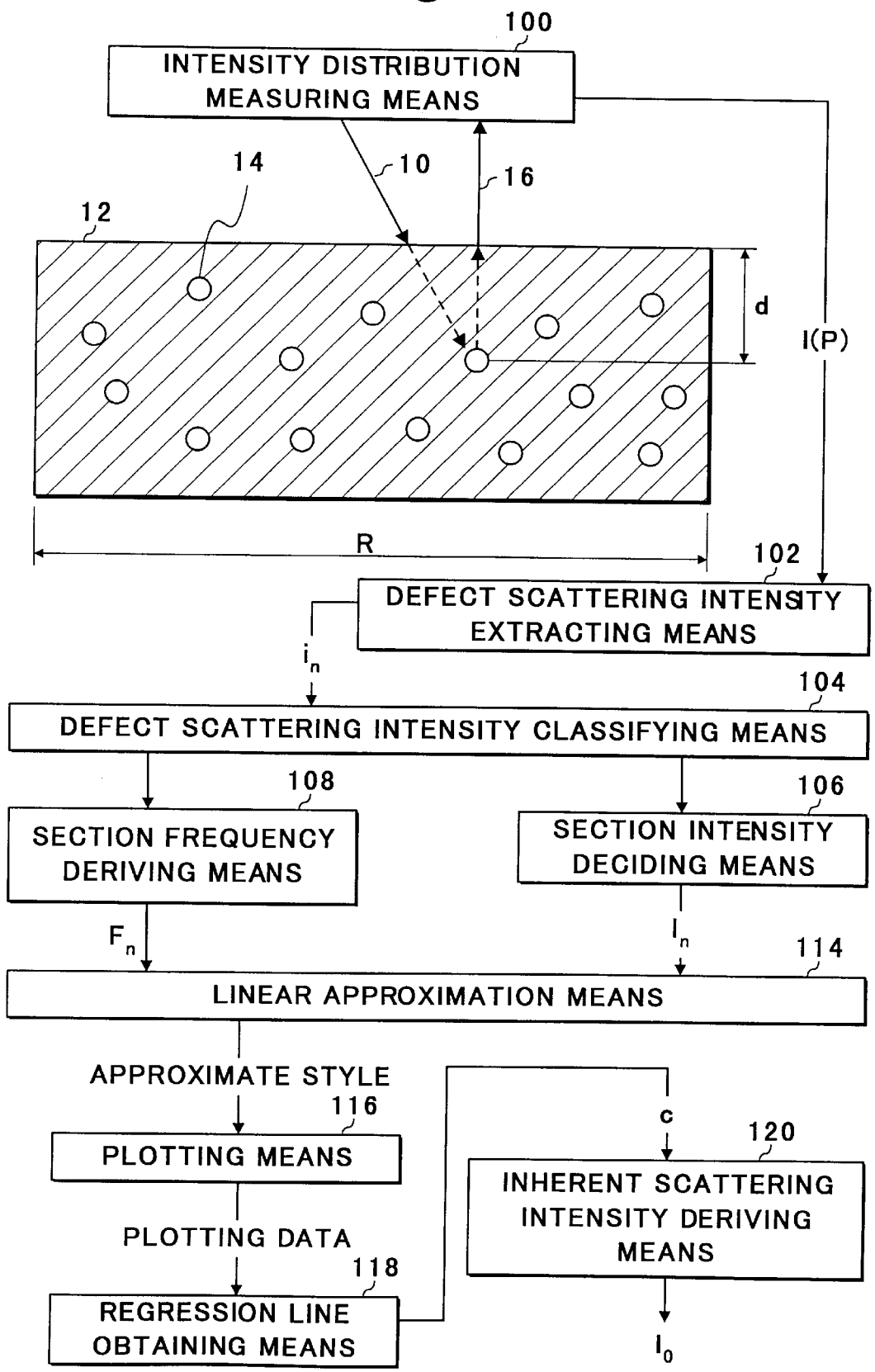
FIG. 11 is a conception diagram which shows the construction of the apparatus for measuring a defect inherent scattering intensity in accordance with the third mode of this invention.

FIG. 11 is a conception diagram which shows the construction of the apparatus for measuring a defect inherent scattering intensity in accordance with the third mode of this invention. Hereafter, the construction of the third mode of this invention is explained by using this figure.

As shown in this figure, the apparatus for measuring a defect inherent scattering intensity in accordance with the third mode of this invention comprises the inherent scattering intensity deriving means 120 in stead of the defect density deriving means 112 of the apparatus for measuring a defect density of the second mode of this invention. Other compositions are the same as the second mode. Here, the linear approximation means 114 uses the approximate style of "y=ax+b".

Figure 12:
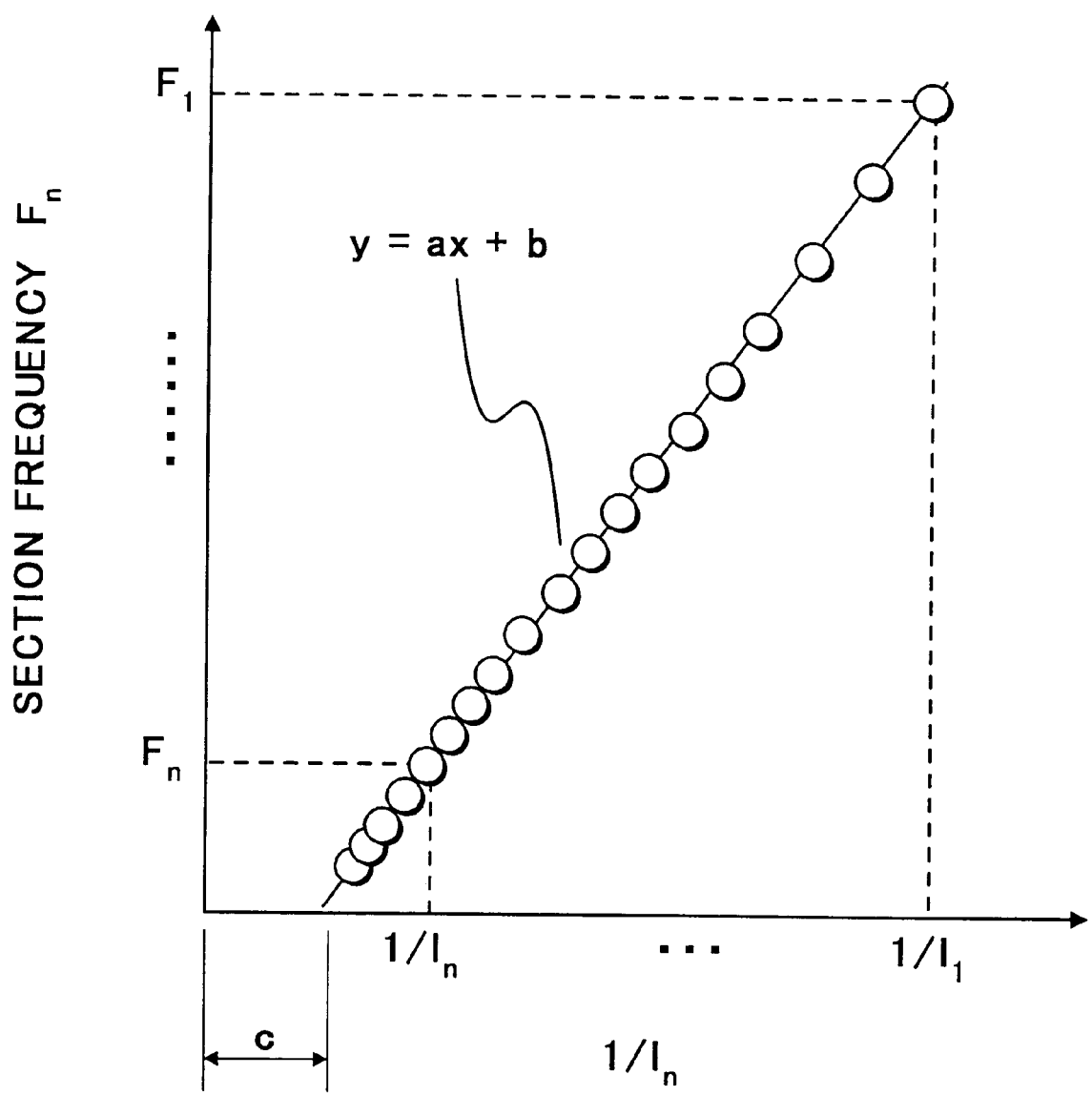
FIG. 12 is a conception diagram which shows the plotting data obtained by using the differentiation type deriving method and linear approximation by which the y-intercept is considered and shows the regression line of the plotting data.

FIG. 12 is a conception diagram which shows the plotting data obtained by using the differentiation type deriving method and linear approximation by which the y-intercept is considered and shows the regression line of the plotting data. As shown in this figure, the x-intercept exists on the regression line obtained by the regression line obtaining means 118 if the style of "y=ax+b" is used.

The inherent scattering intensity deriving means 120 derives the inherent scattering intensity $I_0$ of the defect 14 by using the x-intercept. The inherent scattering intensity $I_0$ of the defect 14 can be obtained by performing the following steps.

(1) Assuming that the inherent scattering intensity $I_0$ is the intensity of the scattered light 16 at zero depth because the inherent scattering intensity $I_0$ of the defect 14 is equivalent to the intensity of the scattered light 16 in case that the laser 10 does not attenuate.

(2) Substituting zero for the $\Delta d_n$ in the following numerical expression, because the attenuation curve 18 of the laser is an exponential curve as shown expression 1 and the section depth $\Delta d_n$ is zero when the defect depth is zero.

(Expression 22)

$$F_n = \Delta d_n \cdot S \cdot \rho \quad (22)$$

Here, it can be thought that the section frequency $F_n$ is zero when the section depth $\Delta d_n$ is zero because the area S of the measuring region R and the defect density $\rho$ have the certain values.

(3) Therefore, expressing the x-intercept shown in FIG. 12 as the following numerical expression because the section frequency $F_n$ is zero when the scattering intensity is equal to the inherent scattering intensity $I_0$.

(Expression 27)

$$c = \frac{1}{I_0} \quad (27)$$

In the above expression, c is the x-intercept of the regression line. And deriving the following numerical expression by expanding the above expression in the shape of "$I_0$=".

(Expression 10)

$$I_0 = \frac{1}{c} \quad (10)$$

The inherent scattering intensity deriving means 120 assumes the value obtained by solving the above expression to the inherent scattering intensity $I_0$ of the defect 14.

Incidentally, though the plotting data and the regression line of the differentiation type are shown in FIG. 12, the third mode of this invention can be constructed by using the difference type.

The apparatus for measuring a defect inherent scattering intensity in accordance with the third mode of this invention can be constructed as a method of measuring a defect inherent scattering intensity.

Figure 13:
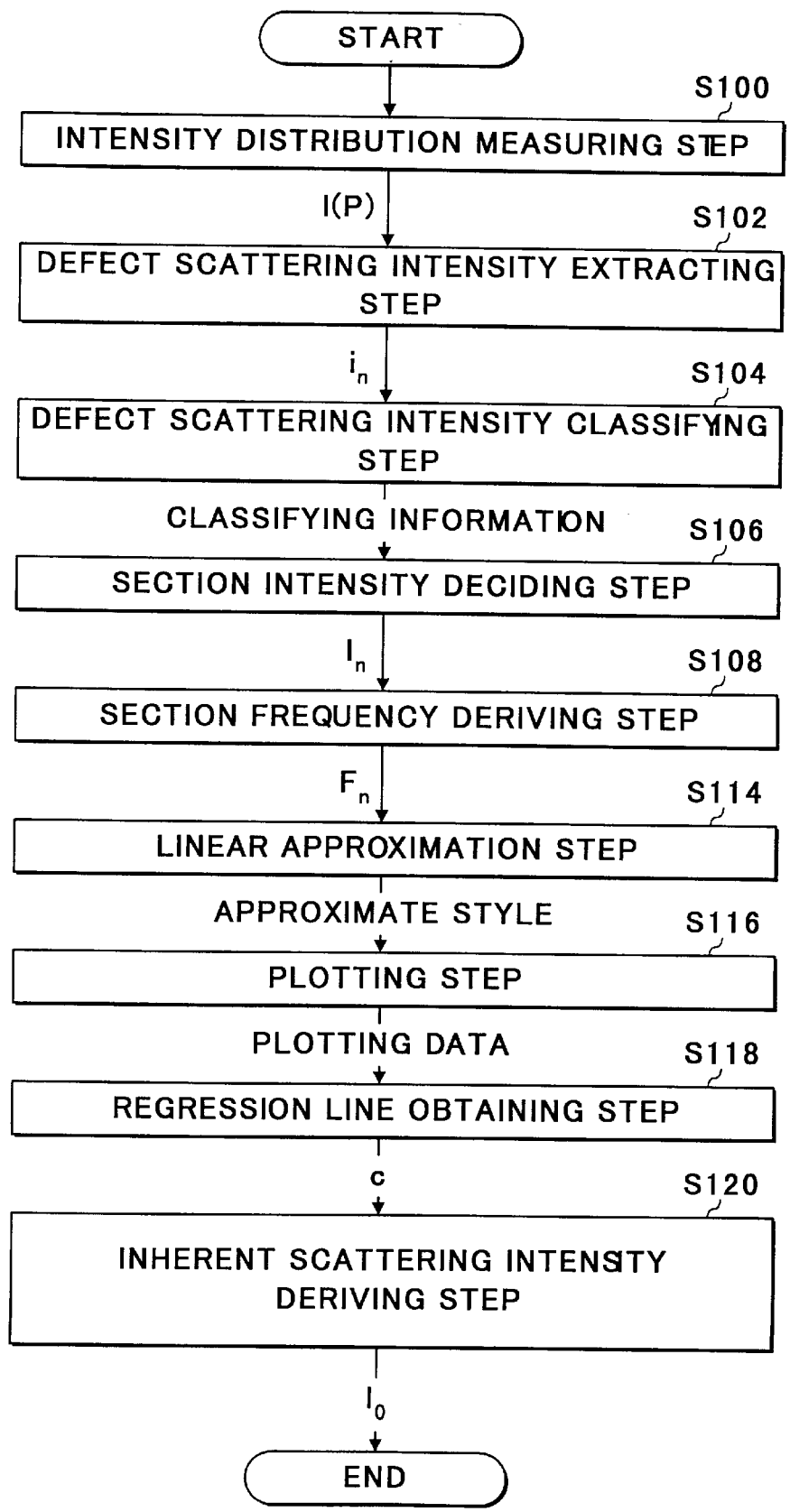
FIG. 13 is a flow chart which shows the construction of the method of measuring a defect inherent scattering intensity in accordance with the third mode of this invention.

FIG. 13 is a flow chart which shows the construction of the method of measuring a density of defects in accordance with the third mode of this invention. Hereafter, the construction of the method of measuring a defect inherent scattering intensity in accordance with the third mode of this invention is explained by using this figure.

The intensity distribution measuring step S100 corresponds to the intensity distribution measuring means 100, in the same way, the defect scattering intensity extracting step S102 corresponds to the defect scattering intensity extracting means 102, the defect scattering intensity classifying step S104 corresponds to the defect scattering intensity classifying means 104, the section intensity deciding step S106 corresponds to the section intensity deciding means 106, the section frequency deriving step S108 corresponds to the section frequency deriving means 108, the linear approximation step S114 corresponds to the linear approximation means 114, the plotting step S116 corresponds to the plotting means 116, the regression line obtaining step S118 corresponds to the regression line obtaining means 118, and the inherent scattering intensity deriving step S120 corresponds to the inherent scattering intensity deriving means 120.

The construction shown in this figure is performed as the following steps.

(1) Irradiating the laser 10 to the surface of the semiconductor 12 (intensity distribution measuring step S100).

(2) Receiving the scattered light 16 emitted from the surface of the semiconductor 12 by irradiating the laser 10 (intensity distribution measuring step S100).

(3) Repeating the step 1 and step 2 while the irradiating position of the laser 10 is varied, and measuring the intensity distribution of the measuring region R by scanning in the measuring region R (intensity distribution measuring step S100).

(4) Extracting the defect scattering intensities 36 from the intensity distribution measured in the intensity distribution measuring step S100 (defect scattering intensity extracting step S102).

(5) Classifying the defect scattering intensities 36 extracted in the defect scattering intensity extracting step S102 with the section range $\Delta I$ (defect scattering intensity classifying step S104).

(6) Deciding the section intensities based on the classifying result in the defect scattering intensity classifying step S104 (section intensity deciding step S106).

(7) Deriving the section frequencies based on the classifying result in the defect scattering intensity classifying step S104 (section frequency deriving step S108).

(8) Applying the linear approximation to the section frequencies $F_n$ in the style of "y=ax+b" (linear approximation step S114).

(9) Obtaining the coordinate on the xy plane based on the approximate result obtained in the linear approximation step S114. That is, the values obtained by executing expression 5 or expression 8 are plotted on the x axis of the xy plane, and the section frequencies are plotted on the y axis of the xy plane (plotting step S116).

(10) Obtaining the regression line of the data plotted on the sy plane in the plotting step S116 (regression line obtaining step S118).

(11) Obtaining the x-intercept of the regression line obtained in the regression line obtaining step S118, and calculating the inherent scattering intensity $I_0$ by substituting the obtained x-intercept for expression 10 (inherent scattering intensity deriving step S120).

According to the third mode of this invention, the inherent scattering intensity $I_0$ of the defect 14 can be obtained.

DESCRIPTION OF THE PREFERRED EMBODIMENT

Figure 14:
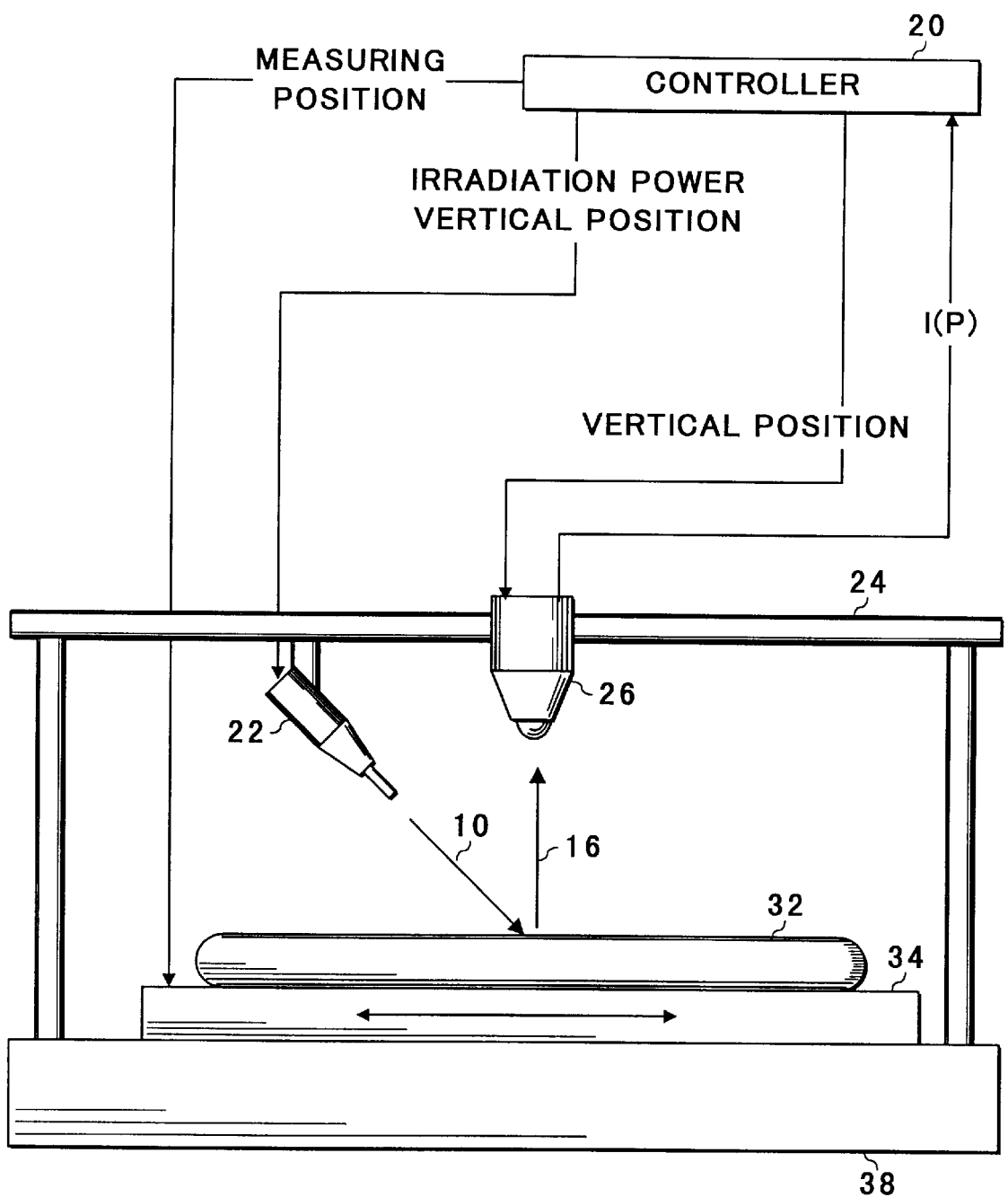
FIG. 14 is a side view which shows the construction of the apparatus for measuring defects in accordance with the preferred embodiment of this invention.

FIG. 14 is a side view which shows the construction of the apparatus for measuring defects in accordance with the preferred embodiment of this invention. Hereafter, the construction of this apparatus for measuring defects is explained by using this figure.

The irradiation device 22 is the device which irradiates the laser 10 to the surface of the semiconductor wafer 32. This irradiation device 22 is fixed to the frame 24 in a state where vertical motion can be possible, and irradiates the laser 10 to the surface of the semiconductor wafer 32 from a fixed distance at a fixed angle. The power of the laser 10 is indicated by the controller 20.

The receiving device (photo detector) 26 is the device which receives the scattered light 16 emitted from the surface of the semiconductor wafer 32. This receiving device 26 is fixed to the frame 24 in a state where vertical motion can be possible, and receives the scattered light from the surface of the semiconductor wafer 32 from a fixed distance. The intensity of the scattered light received by the receiving device 26 is output to the controller 20.

The stage 34 mounts the semiconductor wafer 32 thereon, and moves on the base 38 in the direction of XY according to the instruction of the controller 20 together with the semiconductor wafer 32. The moving position of the stage 34 is output to the controller 20.

The controller 20 instructs the irradiation power of the laser 10, vertical movement of the irradiation device 22, vertical movement of the receiving device 26 and moving direction of the stage 34, and receives the intensity of the scattered light from the receiving device 26 and moving position of the stage 34 from the stage 34, and then executes a fixed calculation.

Hereafter, the actions of the apparatus for measuring defects constructed like the above are explained.

The controller 20 directs the irradiation power of the laser 10 and the vertical position of the irradiation device 22 to the irradiation device 22, and directs the vertical position of the receiving device 26 to the receiving device 26, and directs the measuring position to the stage 34. The irradiation device 22 and the receiving device 26 which have been the vertical positions from the controller 20 move the received positions, and then stop at the positions where they are separated fixed distances between the semiconductor wafer 32 respectively. At the same time, the stage 34 received the measuring position from the controller 20 moves the received position together with the semiconductor wafer 32, and outputs the moved position to the controller 20.

Subsequently, the irradiation device 22 irradiates the laser 10 to the surface of the semiconductor wafer 32 at the irradiation power received from the controller 20. The receiving device 26 receives the scattered light 16 emitted from the surface of the semiconductor wafer 32 by laser irradiation of the irradiation device 22, outputs the intensity of the scattered light 16 to the controller 20.

The controller 20 memorizes the scattered light 16 received from the receiving device 26 and the measuring position received from the stage 34, and then outputs the next measuring position to the stage 34. A fixed region of the semiconductor wafer 32 has been scanned by repeating the above actions.

The controller 20 extracts the defect scattering intensities from the intensities of the scattered light 16 received from the receiving device 26 after scanning the semiconductor wafer 32. And the defect scattering intensities which have been extracted are classified by the section range $\Delta I$, and the frequencies of the defects in each of the classified sections are obtained.

Figure 15:
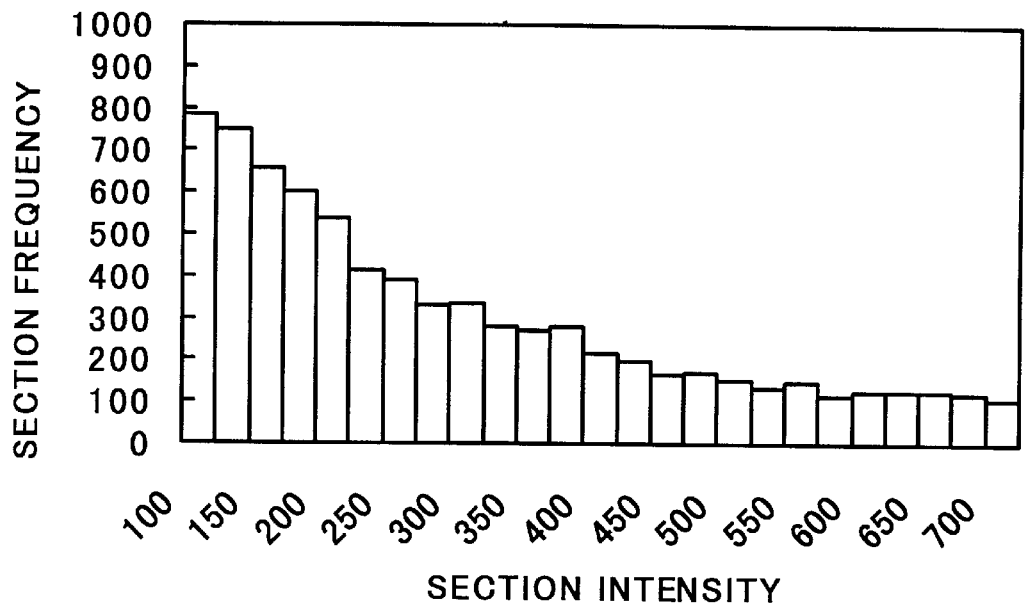
FIG. 15 is a graph which shows an example of the histogram produced by the controller 20 shown in FIG. 14.

FIG. 15 is a graph which shows an example of the histogram produced by the controller 20 shown in FIG. 14. When the frequencies of the defects which controller 20 obtains is shown by the histogram, they become as shown in this figure.

Next, the controller 20 selects the differentiation type or the difference type as the processing method of the attenuation curve 18 of the laser 10, and plots the plotting data consist of x points obtained by solving the following numerical expression and y points which are the section frequencies $F_n$ on the xy plane in case that the differentiation type is selected.

(Expression 5)

$$x = \frac{1}{I_n} \tag{5}$$

In the above expression, $I_n$ are the section intensities on the x axis of the histogram shown in FIG. 15.

When the difference type is selected, the values obtained by solving the following numerical expression are plotted on the x axis of the xy plane, and the section frequencies $F_n$ are plotted on the y axis of the xy plane.

(Expression 8)

$$x = \frac{I_n}{I_n - \Delta I} \tag{8}$$

In the above expression, $I_n$ are the section intensities on the x axis of the histogram shown in FIG. 15, and $\Delta I$ is the section range of the histogram.

Subsequently, the controller 20 selects the style of "y=ax" or "y=ax+b", and obtains the regression line from the date plotted on the xy plane.

Figure 16:
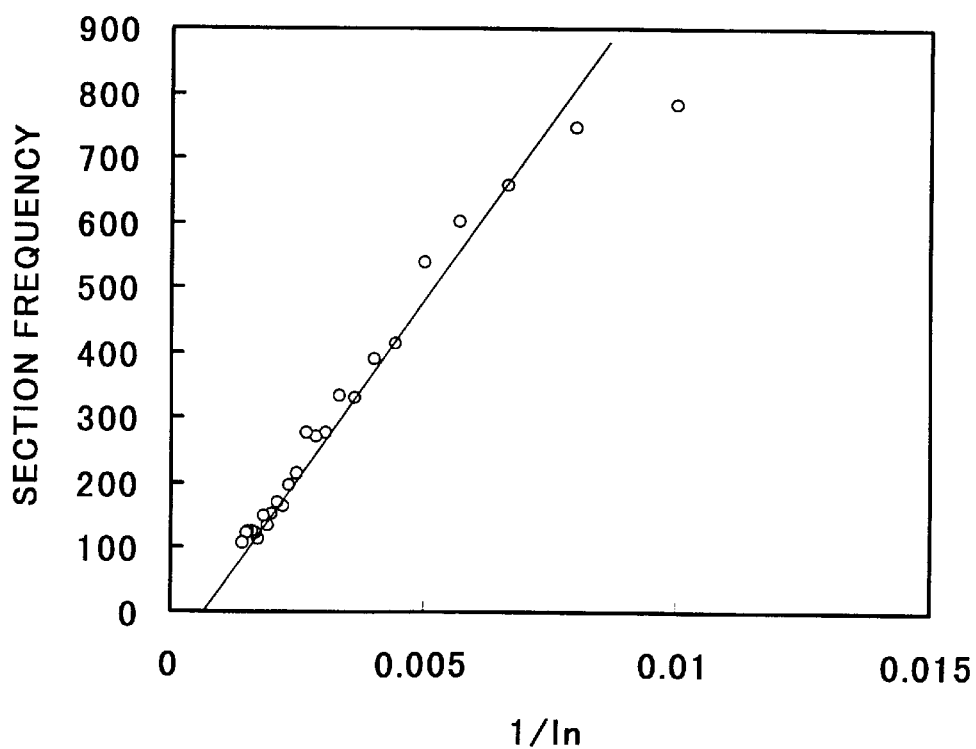
FIG. 16 is a graph which shows an example of the differentiation type plotting data and regression line obtained by selecting the style of "y=ax+b".

FIG. 16 is a graph which shows an example of the differentiation type plotting data and regression line obtained by selecting the style of "y=ax+b".

Next, the gradient a' is obtained, and then the following numerical expression is executed.

(Expression 6)

$$\rho = \frac{2a'}{\alpha \cdot S \cdot \Delta I} \tag{6}$$

The controller 20 displays the value obtained by solving the above expression as the defect density $\rho$.

Subsequently, the x-intercept c of the regression line shown in this figure is obtained, and the following numerical expression is executed.

(Expression 10)

$$I_0 = \frac{1}{c} \qquad (10)$$

The controller 20 displays the value as the inherent scattering intensity $I_0$.

On the other hand, the case that the controller 20 selects the style of "y=ax" is explained as follows.

Figure 17:
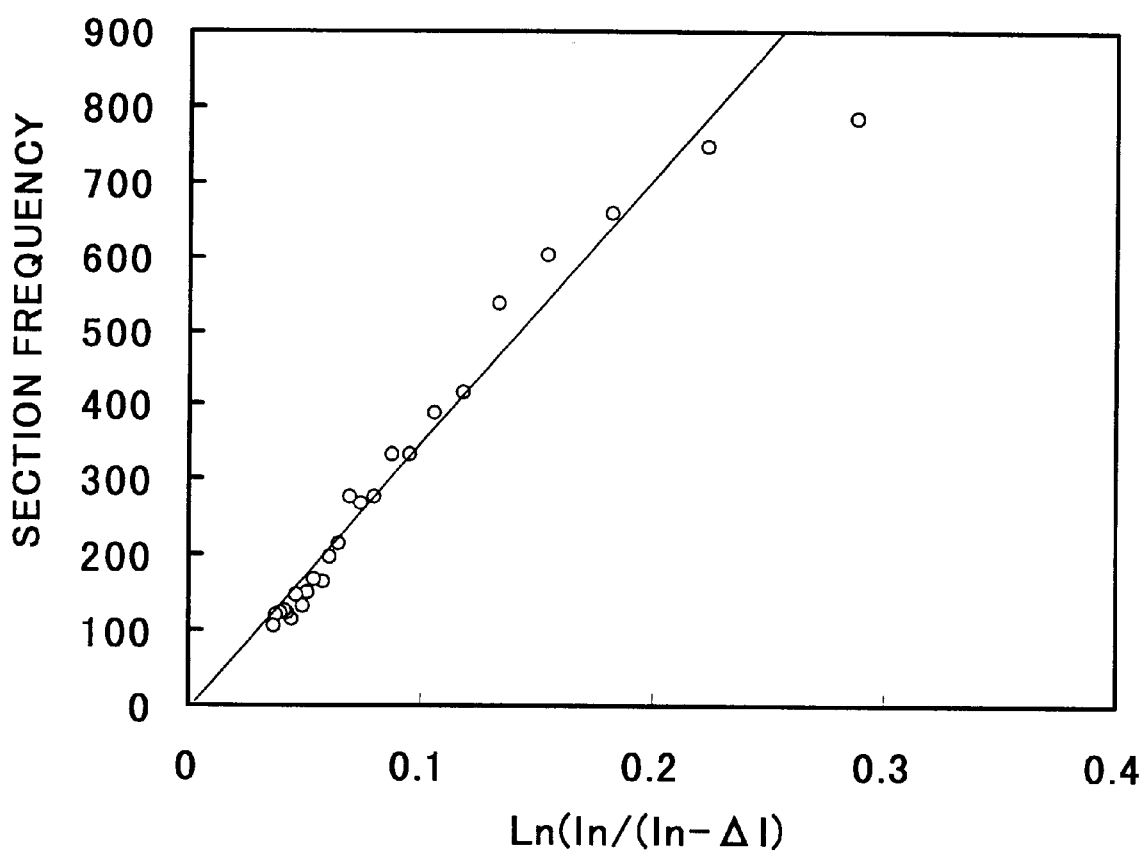
FIG. 17 is a graph which shows an example of the difference type plotting data and regression line obtained by selecting the style of "y=ax".

FIG. 17 is a graph which shows an example of the difference type plotting data and regression line obtained by selecting the style of "y=a+b". The controller 20 obtains the gradient a' of the regression line shown in this figure, and executes the following numerical expression.

(Expression 9)

$$\rho = \frac{2a'}{\alpha \cdot S} \qquad (9)$$

And the controller 20 displays the value obtained by solving the above expression as the defect density $\rho$.

The defect density $\rho$ of the semiconductor wafer 32 and the inherent scattering intensity of the defect existing in the semiconductor wafer 32 are measured by performing the above steps.

Finally, the defect density measured by the above embodiment was compared with the defect density measured by the laser scattering tomography.

Figure 18:
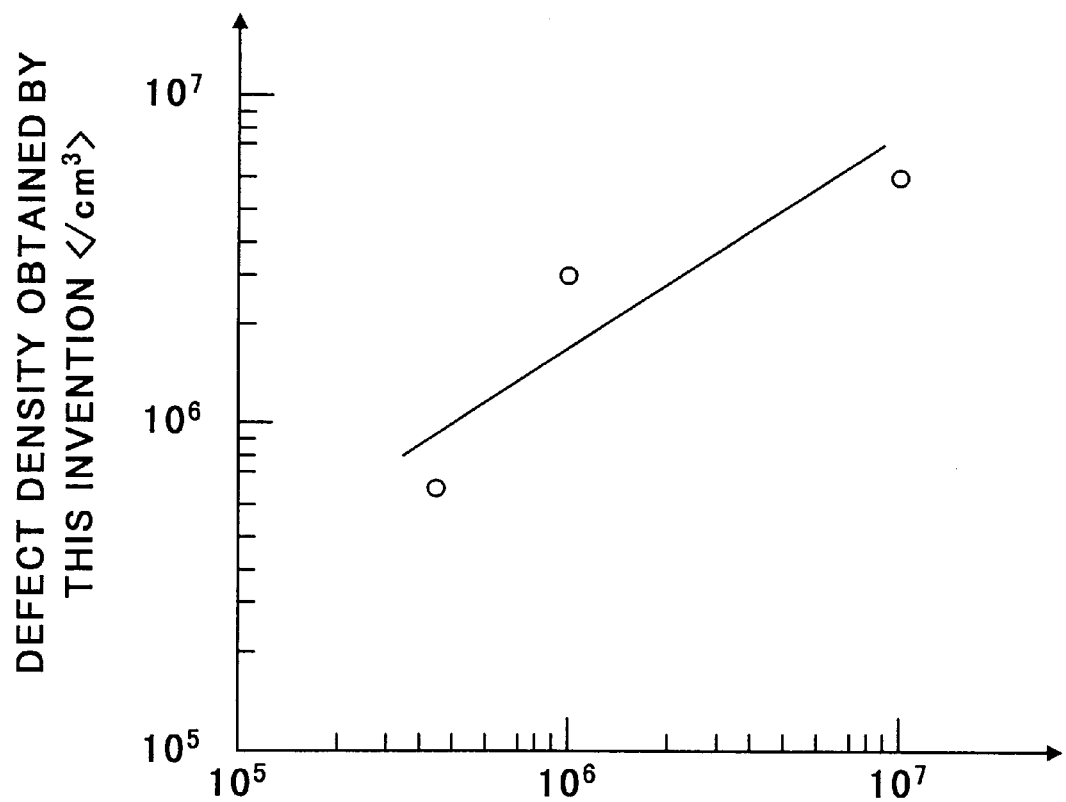
FIG. 18 is a graph which shows the correlate between the densities of the defects measured by the preferred embodiment of this invention and those of measuring by the laser scattering tomography.

FIG. 18 is a graph which shows the correlate between the densities of the defects measured by the preferred embodiment of this invention and those of measuring by the laser scattering tomography. As shown in this figure, both of the values correspond by 1:1. Therefore, according to this invention, the accurate measurement of the defect density can be expected.

This invention may be embodied in other specific forms without departing from the spirit or essential characteristics thereof. The present embodiment is therefore to be considered in all respects as illustrative and not restrictive, the scope of this invention being indicated by the appended claims rather than by the foregoing description and all changes which come within the meaning and range of equivalency of the claims are therefore intended to be embraced therein.

What is claimed is:

1. An apparatus for measuring a defect density of defects existing in a semiconductor, comprising:

intensity distribution measuring means for scanning a measuring region of the semiconductor by a laser, and measuring a intensity distribution of a scattering light obtained from the measuring region;

defect scattering intensity extracting means for extracting a defect scattering intensity from the intensity distribution measured by the intensity distribution measuring means;

defect scattering intensity classifying means for classifying the defect scattering intensity extracted by the defect scattering intensity extracting means into plural sections with a section range;

section intensity deciding means for deciding section intensities in each of the sections classified by the defect scattering intensity classifying means;

section frequency deriving means for deriving section frequencies in each of the sections classified by the defect scattering intensity classifying means;

section depth deriving means for applying the section intensities decided by the section intensity deciding means to a attenuation curve of the laser, and deriving section depths in each of the sections; and defect density deriving means for deriving the defect density by using the section frequencies derived by the section frequency deriving means and the section depths derived by the section depth deriving means.

2. An apparatus for measuring a defect density of defects existing in a semiconductor, as claimed in claim 1, wherein the attenuation curve is expressed as a following numerical expression (Expression 1)

$$I(d) = I_0 \cdot \exp\left(-\frac{2}{\alpha} \cdot d\right) \qquad (1)$$

where I(d) is an intensity of the scattered light obtained from the defect existing in depth d, $I_0$ is an inherent scattering intensity of the defect, d is a depth where the defect exists, and $\alpha$ is a penetration depth of the laser; and the section depth deriving means executes a following numerical expression (Expression 2)

$$\Delta d_n = \frac{\alpha \cdot \Delta I}{2 \cdot I_n} \qquad (2)$$

where $\Delta d_n$ are the section depths, $\alpha$ is the penetration depth, $\Delta I$ is the section range, and $I_n$ are the section intensities.

3. An apparatus for measuring a defect density of defects existing in a semiconductor, as claimed in claim 1, wherein the attenuation curve is expressed as a following numerical expression (Expression 1)

$$I(d) = I_0 \cdot \exp\left(-\frac{2}{\alpha} \cdot d\right) \qquad (1)$$

where I(d) is an intensity of the scattered light obtained from the defect existing in depth d, $I_0$ is an inherent scattering intensity of the defect, d is a depth where the defect exists, and $\alpha$ is a penetration depth of the laser; and the section depth deriving means executes a following numerical expression (Expression 3)

$$\Delta d_n = \frac{\alpha}{2} \cdot \text{Ln} \cdot \left(\frac{I_n}{I_n - \Delta I}\right) \qquad (3)$$

where $\Delta d_n$ are the section depths, $\alpha$ is the penetration depth, $I_n$ are the section intensities, and $\Delta I$ is the section range.

4. An apparatus for measuring a defect density of defects existing in a semiconductor, comprising:

intensity distribution measuring means for scanning a measuring region of the semiconductor by a laser, and measuring a intensity distribution of a scattering light obtained from the measuring region;

defect scattering intensity extracting means for extracting a defect scattering intensity from the intensity distribution measured by the intensity distribution measuring means;

defect scattering intensity classifying means for classifying the defect scattering intensity extracted by the defect scattering intensity extracting means into plural sections with a section range;

section intensity deciding means for deciding section intensities in each of the sections classified by the defect scattering intensity classifying means;

section frequency deriving means for deriving section frequencies in each of the sections classified by the defect scattering intensity classifying means;

linear approximation means for applying the section intensities decided by the section intensity deciding means to a attenuation curve of the laser, and approximating the section frequencies derived by the section frequency deriving means linear;

plotting means for plotting an approximate result by the linear approximation means as plural plotting data on xy plane;

regression line obtaining means for obtaining a regression line of the plotting data plotted by the plotting means; and defect density deriving means for deriving the defect density by using a gradient of the regression line obtained by the regression line obtaining means.

5. An apparatus for measuring a defect density of defects existing in a semiconductor, as claimed in claim 4, wherein the attenuation curve is expressed as a following numerical expression (Expression 1)

$$I(d) = I_0 \cdot \exp\left(-\frac{2}{\alpha} \cdot d\right) \tag{1}$$

where I(d) is an intensity of the scattered light obtained from the defect existing in depth d, $I_0$ is an inherent scattering intensity of the defect, d is a depth where the defect exists, and α is a penetration depth of the laser;

the linear approximation means approximates the section frequencies based on a following numerical expression (Expression 4)

$$y = ax + b \tag{4}$$

where a is a gradient and b is a y-intercept;

the plotting means plots values obtained by solving a following numerical expression on x axis of the xy plane, and plots the section frequencies on y axis of the xy plane (Expression 5)

$$x = \frac{1}{I_n} \tag{5}$$

where $I_n$ are the section intensities; and the defect density deriving means executes a following numerical expression (Expression 6)

$$\rho = \frac{2a'}{\alpha \cdot S \cdot \Delta I} \tag{6}$$

where ρ is the defect density, a' is the gradient of the regression line, α is the penetration depth, S is an area of the measuring region, and ΔI is the section range.

6. An apparatus for measuring a defect density of defects existing in a semiconductor, as claimed in claim 4, wherein the attenuation curve is expressed as a following numerical expression (Expression 1)

$$I(d) = I_0 \cdot \exp\left(-\frac{2}{\alpha} \cdot d\right) \tag{1}$$

where I(d) is an intensity of the scattered light obtained from the defect existing in depth d, $I_0$ is an inherent scattering intensity of the defect, d is a depth where the defect exists, and α is a penetration depth of the laser;

the linear approximation means approximates the section frequencies based on a following numerical expression (Expression 7)

$$y = ax \tag{7}$$

where a is a gradient;

the plotting means plots values obtained by solving a following numerical expression on x axis of the xy plane, and plots the section frequencies on y axis of the xy plane (Expression 8)

$$x = \frac{I_n}{I_n - \Delta I} \tag{8}$$

where $I_n$ are the section intensities and ΔI is the section range; and the defect density deriving means executes a following numerical expression (Expression 9)

$$\rho = \frac{2a'}{\alpha \cdot S} \tag{9}$$

where ρ is the defect density, a' is the gradient of the regression line, α is the penetration depth, and S is an area of the measuring region.

7. An apparatus for measuring an inherent scattering intensity of defects existing in a semiconductor, comprising:

intensity distribution measuring means for scanning a measuring region of the semiconductor by a laser, and measuring a intensity distribution of a scattering light obtained from the measuring region;

defect scattering intensity extracting means for extracting a defect scattering intensity from the intensity distribution measured by the intensity distribution measuring means;

defect scattering intensity classifying means for classifying the defect scattering intensity extracted by the defect scattering intensity extracting means into plural sections with a section range;

section intensity deciding means for deciding section intensities in each of the sections classified by the defect scattering intensity classifying means;

section frequency deriving means for deriving section frequencies in each of the sections classified by the defect scattering intensity classifying means;

linear approximation means for applying the section intensities decided by the section intensity deciding means to a attenuation curve of the laser, and approximating the section frequencies derived by the section frequency deriving means linear;

plotting means for plotting an approximate result by the linear approximation means as plural plotting data on xy plane;

regression line obtaining means for obtaining a regression line of the plotting data plotted by the plotting means; and inherent scattering intensity deriving means for deriving the inherent scattering intensity by using a x-intercept of the regression line obtained by the regression line obtaining means.

8. An apparatus for measuring an inherent scattering intensity of defects existing in a semiconductor, as claimed in claim 7, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser;

the linear approximation means approximates the section frequencies based on a following numerical expression (Expression 4)

$$y = ax + b \quad (4)$$

where a is a gradient and b is a y-intercept;

the plotting means plots values obtained by solving a following numerical expression on x axis of the xy plane, and plots the section frequencies on y axis of the xy plane (Expression 5)

$$x = \frac{1}{I_n} \quad (5)$$

where $I_n$ are the section intensities; and the inherent scattering intensity deriving means executes a following numerical expression (Expression 10)

$$I_0 = \frac{1}{c} \quad (10)$$

where $I_0$ is the inherent scattering intensity and c is the x-intercept of the regression line.

9. A method of measuring a defect density of defects existing in a semiconductor, comprising:

an intensity distribution measuring step of scanning a measuring region of the semiconductor by a laser, and measuring a intensity distribution of a scattering light obtained from the measuring region;

a defect scattering intensity extracting step of extracting a defect scattering intensity from the intensity distribution measured in the intensity distribution measuring step;

a defect scattering intensity classifying step of classifying the defect scattering intensity extracted in the defect scattering intensity extracting step into plural sections with a section range;

a section intensity deciding step of deciding section intensities in each of the sections classified in the defect scattering intensity classifying step;

a section frequency deriving step of deriving section frequencies in each of the sections classified in the defect scattering intensity classifying step;

a section depth deriving step of applying the section intensities decided in the section intensity deciding step to a attenuation curve of the laser, and deriving section depths in each of the sections; and a defect density deriving step of deriving the defect density by using the section frequencies derived in the section frequency deriving step and the section depths derived in the section depth deriving step.

10. A method of measuring a defect density of defects existing in a semiconductor, as claimed in claim 9, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser; and the section depth deriving step executes a following numerical expression (Expression 2)

$$\Delta d_n = \frac{\alpha \cdot \Delta I}{2 \cdot I_n} \quad (2)$$

where $\Delta d_n$ are the section depths, α is the penetration depth, ΔI is the section range, and $I_n$ are the section intensities.

11. A method of measuring a defect density of defects existing in a semiconductor, as claimed in claim 9, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser; and the section depth deriving step executes a following numerical expression (Expression 3)

$$\Delta d_n = \frac{\alpha}{2} \cdot \mathrm{Ln} \cdot \left(\frac{I_n}{I_n - \Delta I}\right) \quad (3)$$

where $\Delta d_n$ are the section depths, α is the penetration depth, $I_n$ are the section intensities, and ΔI is the section range.

12. A method of measuring a defect density of defects existing in a semiconductor, comprising:

an intensity distribution measuring step of scanning a measuring region of the semiconductor by a laser, and measuring a intensity distribution of a scattering light obtained from the measuring region;

a defect scattering intensity extracting step of extracting a defect scattering intensity from the intensity distribution measured in the intensity distribution measuring step;

a defect scattering intensity classifying step of classifying the defect scattering intensity extracted in the defect scattering intensity extracting step into plural sections with a section range;

a section intensity deciding step of deciding section intensities in each of the sections classified in the defect scattering intensity classifying step;

a section frequency deriving step of deriving section frequencies in each of the sections classified in the defect scattering intensity classifying step;

a linear approximation step of applying the section intensities decided in the section intensity deciding step to a attenuation curve of the laser, and approximating the section frequencies derived in the section frequency deriving step linear;

a plotting step of plotting an approximate result in the linear approximation step as plural plotting data on xy plane;

a regression line obtaining step of obtaining a regression line of the plotting data plotted in the plotting step; and a defect density deriving step of deriving the defect density by using a gradient of the regression line obtained in the regression line obtaining step.

13. A method of measuring a defect density of defects existing in a semiconductor, as claimed in claim 12, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser;

the linear approximation step approximates the section frequencies based on a following numerical expression (Expression 4)

$$y = ax + b \quad (4)$$

where a is a gradient and b is a y-intercept;

the plotting step plots values obtained by solving a following numerical expression on x axis of the xy plane, and plots the section frequencies on y axis of the xy plane (Expression 5)

$$x = \frac{1}{I_n} \quad (5)$$

where $I_n$ are the section intensities; and the defect density deriving step executes a following numerical expression (Expression 6)

$$\rho = \frac{2a'}{\alpha \cdot S \cdot \Delta I} \quad (6)$$

where ρ is the defect density, a' is the gradient of the regression line, α is the penetration depth, S is an area of the measuring region, and ΔI is the section range.

14. A method of measuring a defect density of defects existing in a semiconductor, as claimed in claim 12, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser;

the linear approximation step approximates the section frequencies based on a following numerical expression (Expression 7)

$$y = ax \quad (7)$$

where a is a gradient;

the plotting step plots values obtained by solving a following numerical expression on x axis of the xy plane, and plots the section frequencies on y axis of the xy plane (Expression 8)

$$x = \frac{I_n}{I_n - \Delta I} \quad (8)$$

where $I_n$ are the section intensities and ΔI is the section range; and the defect density deriving step executes a following numerical expression (Expression 9)

$$\rho = \frac{2a'}{\alpha \cdot S} \quad (9)$$

where ρ is the defect density, a' is the gradient of the regression line, α is the penetration depth, and S is an area of the measuring region.

15. A method of measuring an inherent scattering intensity of defects existing in a semiconductor, comprising:

an intensity distribution measuring step of scanning a measuring region of the semiconductor by a laser, and measuring a intensity distribution of a scattering light obtained from the measuring region;

a defect scattering intensity extracting step of extracting a defect scattering intensity from the intensity distribution measured in the intensity distribution measuring step;

a defect scattering intensity classifying step of classifying the defect scattering intensity extracted in the defect scattering intensity extracting step into plural sections with a section range;

a section intensity deciding step of deciding section intensities in each of the sections classified in the defect scattering intensity classifying step;

a section frequency deriving step of deriving section frequencies in each of the sections classified in the defect scattering intensity classifying step;

a linear approximation step of applying the section intensities decided in the section intensity deciding step to a attenuation curve of the laser, and approximating the section frequencies derived in the section frequency deriving step linear;

a plotting step of plotting an approximate result in the linear approximation step as plural plotting data on xy plane;

a regression line obtaining step of obtaining a regression line of the plotting data plotted in the plotting step; and an inherent scattering intensity deriving step of deriving the inherent scattering intensity by using a x-intercept of the regression line obtained in the regression line obtaining step.

16. A method of measuring an inherent scattering intensity of defects existing in a semiconductor, as claimed in claim 15, wherein the attenuation curve is expressed as a following numerical expression (Expression 1)

$$I(d) = I_0 \cdot \exp\left(-\frac{2}{\alpha} \cdot d\right) \quad (1)$$

where I(d) is an intensity of the scattered light obtained from the defect existing in depth d, $I_0$ is an inherent scattering intensity of the defect, d is a depth where the defect exists, and α is a penetration depth of the laser;

the linear approximation step approximates the section frequencies based on a following numerical expression (Expression 4)

$$y = ax + b \quad (4)$$

where a is a gradient and b is a y-intercept;

the plotting step plots values obtained by solving a following numerical expression on x axis of the xy plane, and plots the section frequencies on y axis of the xy plane (Expression 5)

$$x = \frac{1}{I_n} \quad (5)$$

where $I_n$ are the section intensities; and the inherent scattering intensity deriving step executes a following numerical expression (Expression 10)

$$I_0 = \frac{1}{c} \quad (10)$$

where $I_0$ is the inherent scattering intensity and c is the x-intercept of the regression line.

* * * * *